United States Patent [19]

Nakao et al.

[11] Patent Number: 5,222,961
[45] Date of Patent: Jun. 29, 1993

[54] ENDOSCOPIC STAPLING DEVICE AND RELATED STAPLE

[76] Inventors: Naomi Nakao, 303 E. 57th St., New York, N.Y. 10022; Peter J. Wilk, 185 W. End Ave., New York, N.Y. 10023

[21] Appl. No.: 818,161
[22] Filed: Jan. 8, 1992

Related U.S. Application Data

[63] Continuation-in-part of Ser. No. 695,702, May 3, 1991, Pat. No. 5,156,609, which is a continuation-in-part of Ser. No. 456,960, Dec. 28, 1989, Pat. No. 5,015,249, and a continuation-in-part of Ser. No. 543,704, Jun. 26, 1990, Pat. No. 5,049,153.

[51] Int. Cl.$^5$ .............................................. A61B 17/00
[52] U.S. Cl. ................................... 606/143; 606/142; 606/219
[58] Field of Search ............... 606/219, 142, 151, 157, 606/158, 120, 143; 24/457, 543, 562

[56] References Cited

U.S. PATENT DOCUMENTS

| | | | |
|---|---|---|---|
| 643,003 | 2/1900 | Pollock | 606/120 |
| 943,263 | 12/1909 | Morawek . | |
| 1,510,416 | 9/1924 | Pietz . | |
| 2,113,246 | 4/1938 | Wappler . | |
| 2,384,697 | 9/1945 | Riccardi | 606/120 |
| 2,968,041 | 1/1961 | Skold . | |
| 3,378,010 | 4/1968 | Codling . | |
| 3,518,993 | 7/1970 | Blake . | |
| 3,629,912 | 12/1971 | Klopp | 24/457 |
| 3,631,858 | 1/1972 | Ersek | 606/120 |
| 3,698,043 | 10/1972 | Batts | 24/543 |
| 3,777,538 | 12/1973 | Weatherly et al. | 606/142 |
| 3,882,854 | 5/1975 | Hulka et al. . | |
| 3,958,576 | 5/1976 | Komiya . | |
| 3,982,307 | 9/1976 | Smith et al. | 24/543 |
| 4,038,987 | 8/1977 | Komiya . | |
| 4,212,303 | 7/1980 | Nolan | 606/120 |
| 4,367,746 | 1/1983 | Derechinsky . | |
| 4,394,864 | 7/1983 | Sandhaus . | |
| 4,446,865 | 5/1984 | Jewusiak . | |
| 4,485,817 | 12/1984 | Swiggett . | |
| 4,496,090 | 1/1985 | Crevier et al. . | |
| 4,556,058 | 12/1985 | Green | 606/143 |
| 4,576,165 | 3/1986 | Green et al. | 606/143 |
| 4,681,107 | 7/1987 | Kees, Jr. . | |
| 4,706,668 | 11/1987 | Backer . | |
| 4,714,075 | 12/1987 | Krauter . | |
| 4,716,886 | 1/1988 | Schulman et al. | 606/120 |
| 4,735,194 | 4/1988 | Stiegmann . | |
| 4,744,788 | 5/1988 | Mercer, Jr. | 606/157 |
| 4,759,364 | 7/1988 | Boebel . | |
| 4,796,627 | 1/1989 | Tucker . | |
| 4,807,334 | 2/1989 | Blanchard | 24/543 |
| 4,821,721 | 4/1989 | Chin et al. . | |
| 4,835,824 | 6/1989 | Durham et al. | 24/543 |
| 4,841,888 | 6/1989 | Mills et al. . | |
| 4,880,015 | 11/1989 | Nierman . | |
| 4,887,612 | 12/1989 | Esser . | |
| 4,934,364 | 6/1990 | Green | 606/143 |
| 4,945,920 | 8/1990 | Clossick . | |
| 4,971,067 | 11/1990 | Bolduc et al. . | |
| 4,983,176 | 1/1991 | Cushman et al. . | |
| 5,022,126 | 6/1991 | Davis | 24/543 |
| 5,032,127 | 7/1991 | Frazee et al. | 606/143 |

FOREIGN PATENT DOCUMENTS 2330182 1/1975 Fed. Rep. of Germany .

Primary Examiner—Stephen C. Pellegrino
Assistant Examiner—Gary Jackson
Attorney, Agent, or Firm—R. Neil Sudol; Henry D. Coleman

[57] ABSTRACT

A surgical staple, particularly but not exclusively for use in endoscopic or laparoscopic surgery comprises a first leg provided with a first locking element, a second leg provided with a second locking element, and a hinge joining the first leg and the second leg to one another. The first locking element and the second locking element are designed to cooperate with one another to maintain the staple in a closed postfiring configuration. The staple is disposed in a closed prefiring configuration wherein at least one of the first leg, the second leg, the first locking element and the second locking element is deformed to prevent cooperation of the first locking element and the second locking element. The staple legs are provided with latching elements which cooperate with corresponding elements on a forceps jaws to enable a pivoting of the legs alternately away from and towards one another and about the hinge during a staple opening operation. Such latching elements may include loop-shaped eyelets or snap-lock projections such as knobs or cooperating snap-lock-type recesses.

29 Claims, 28 Drawing Sheets

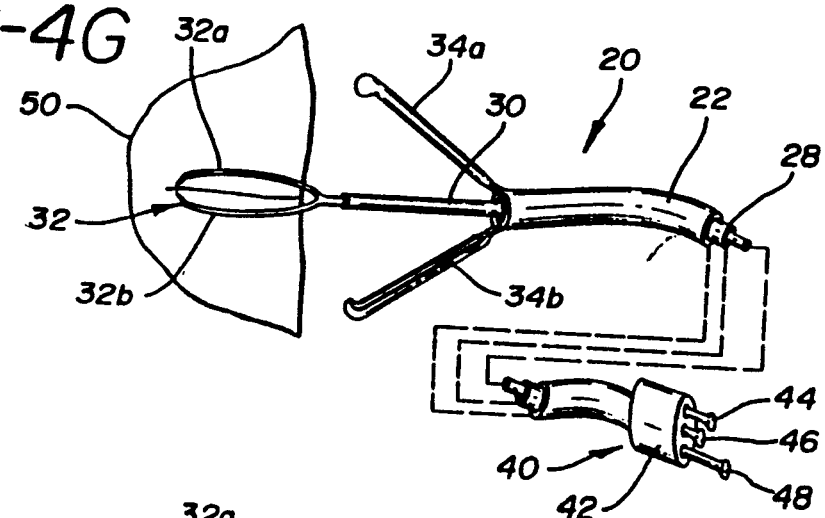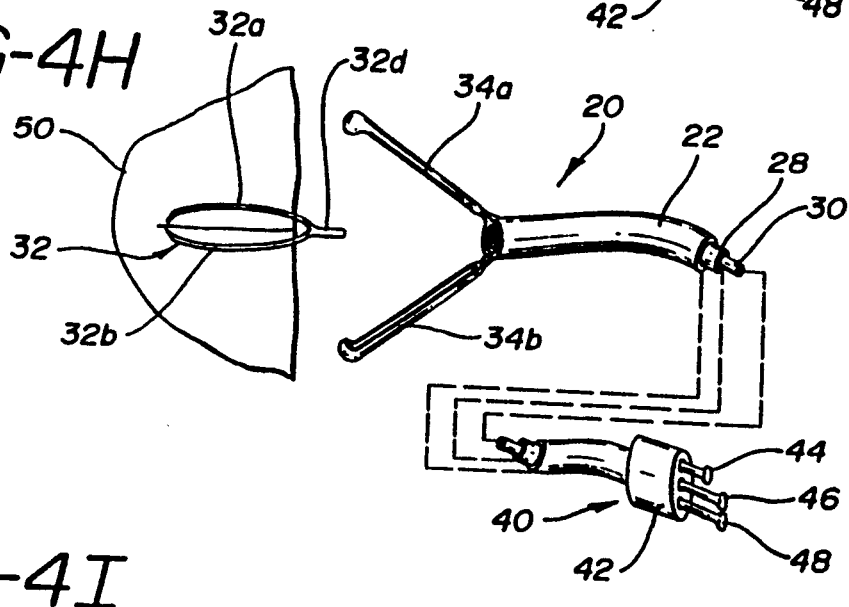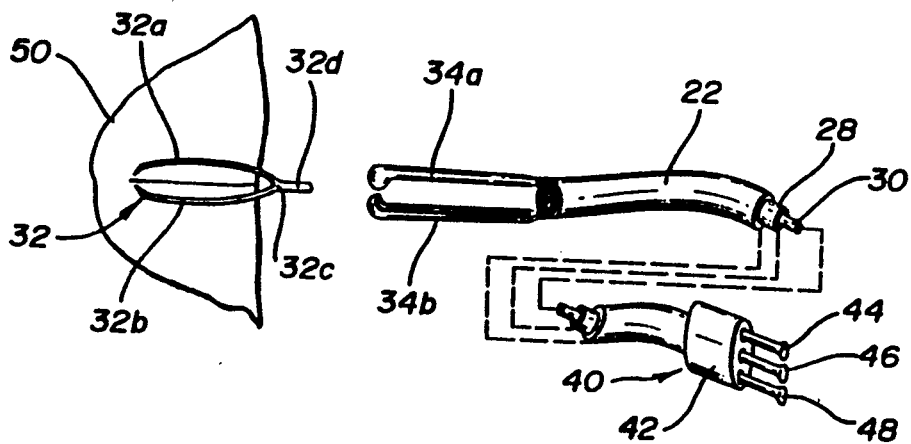

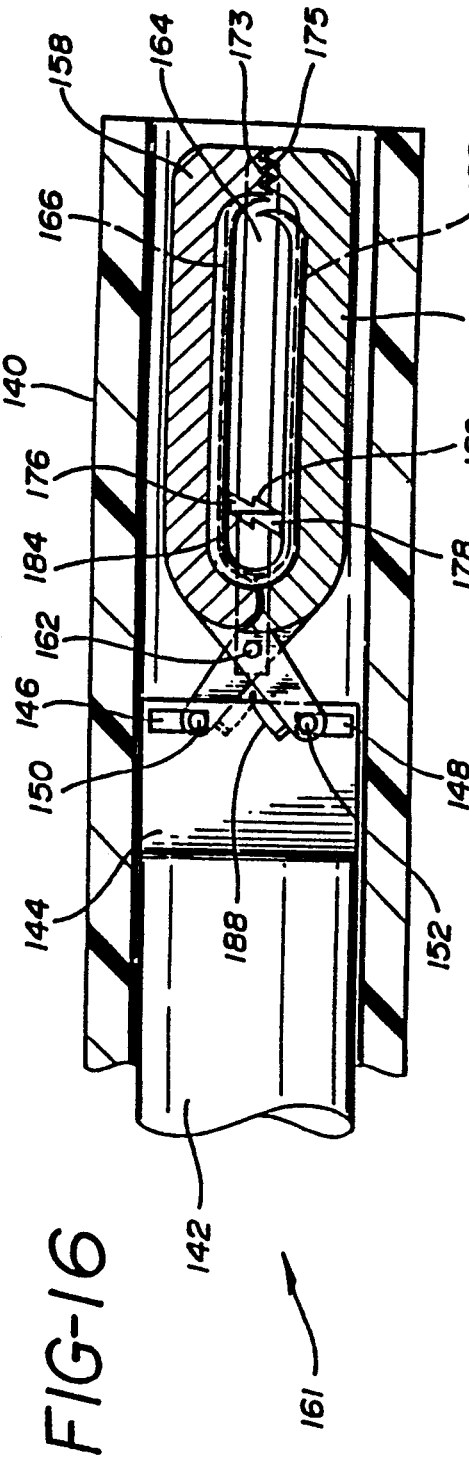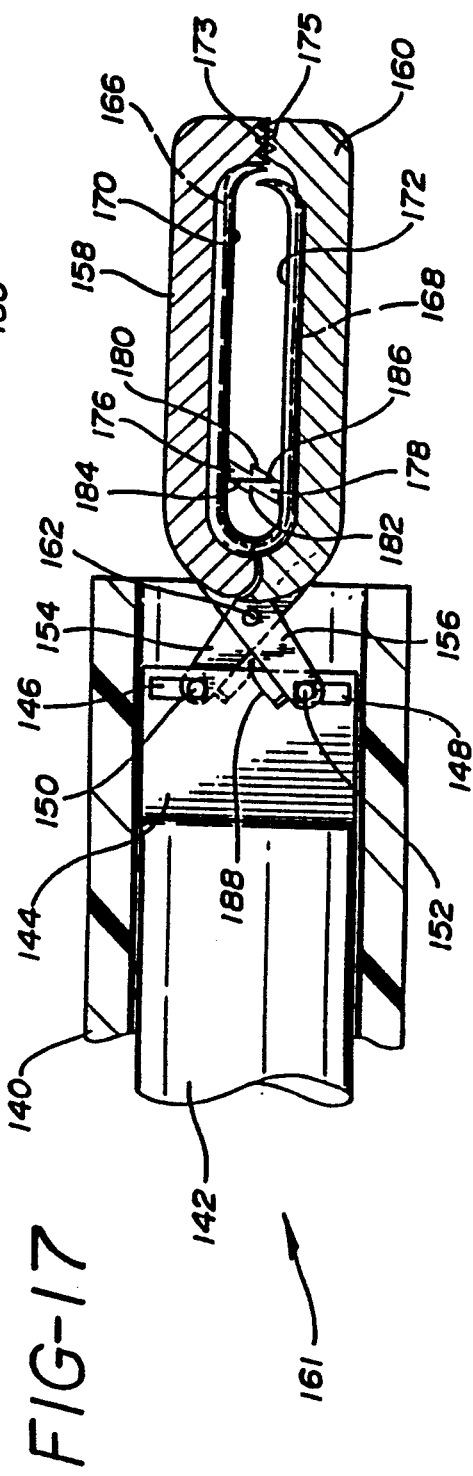

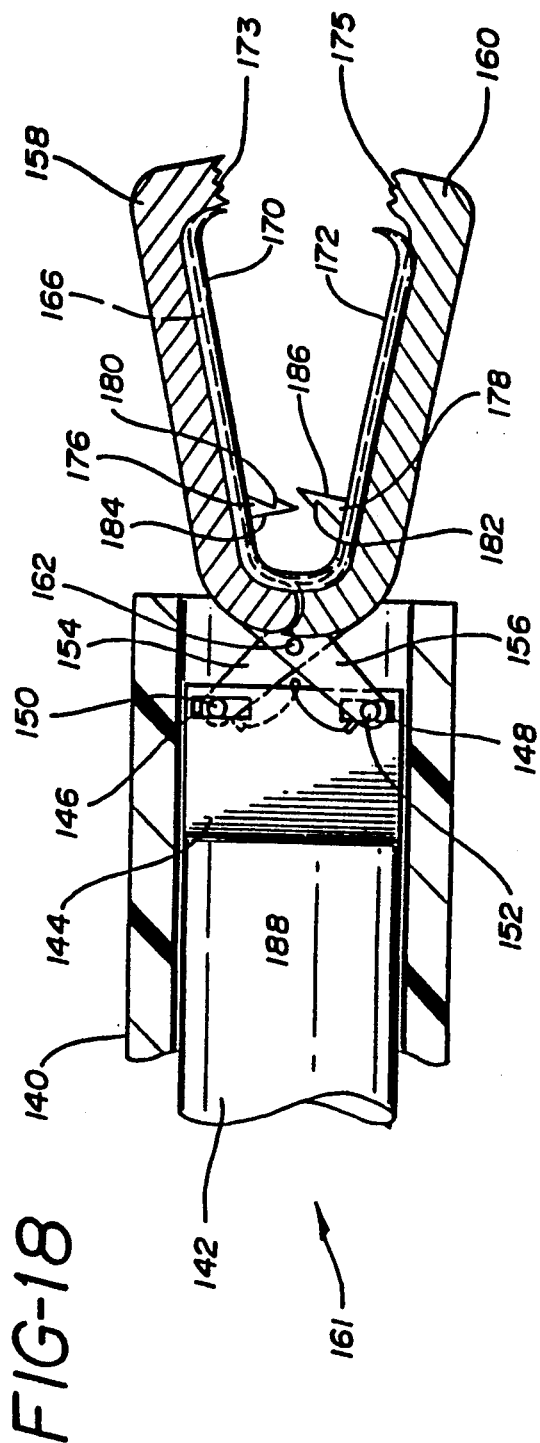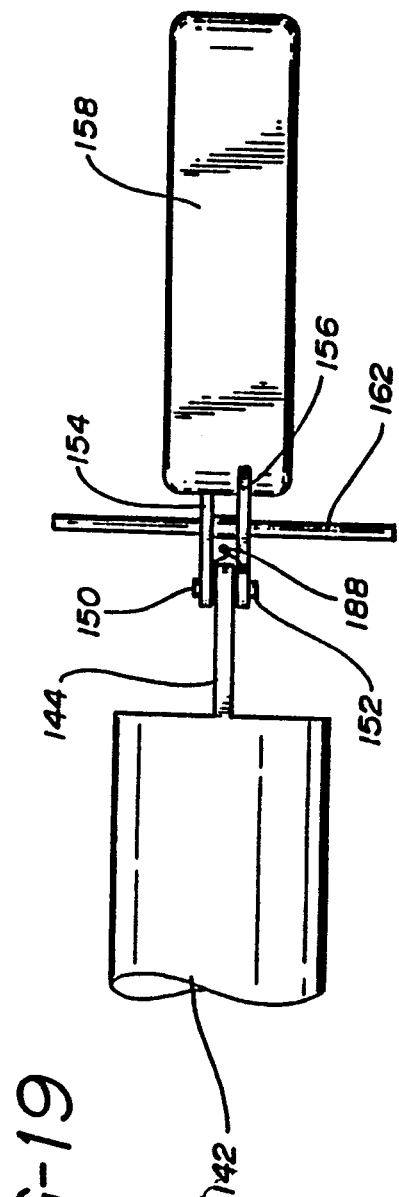

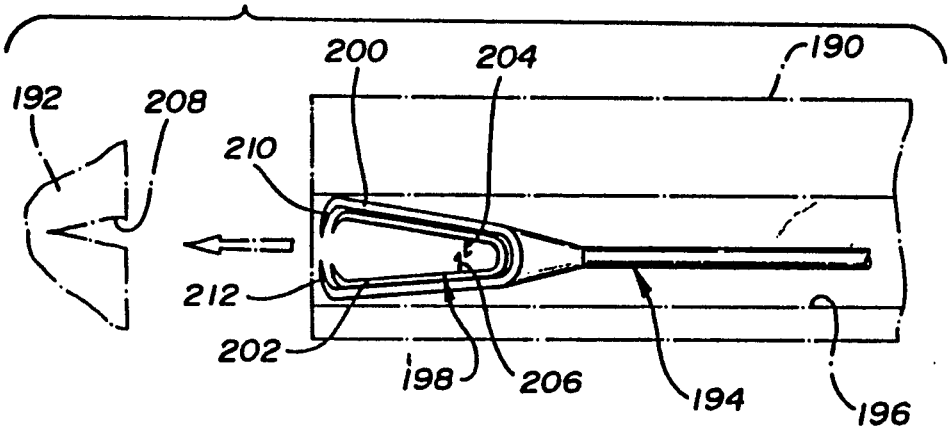

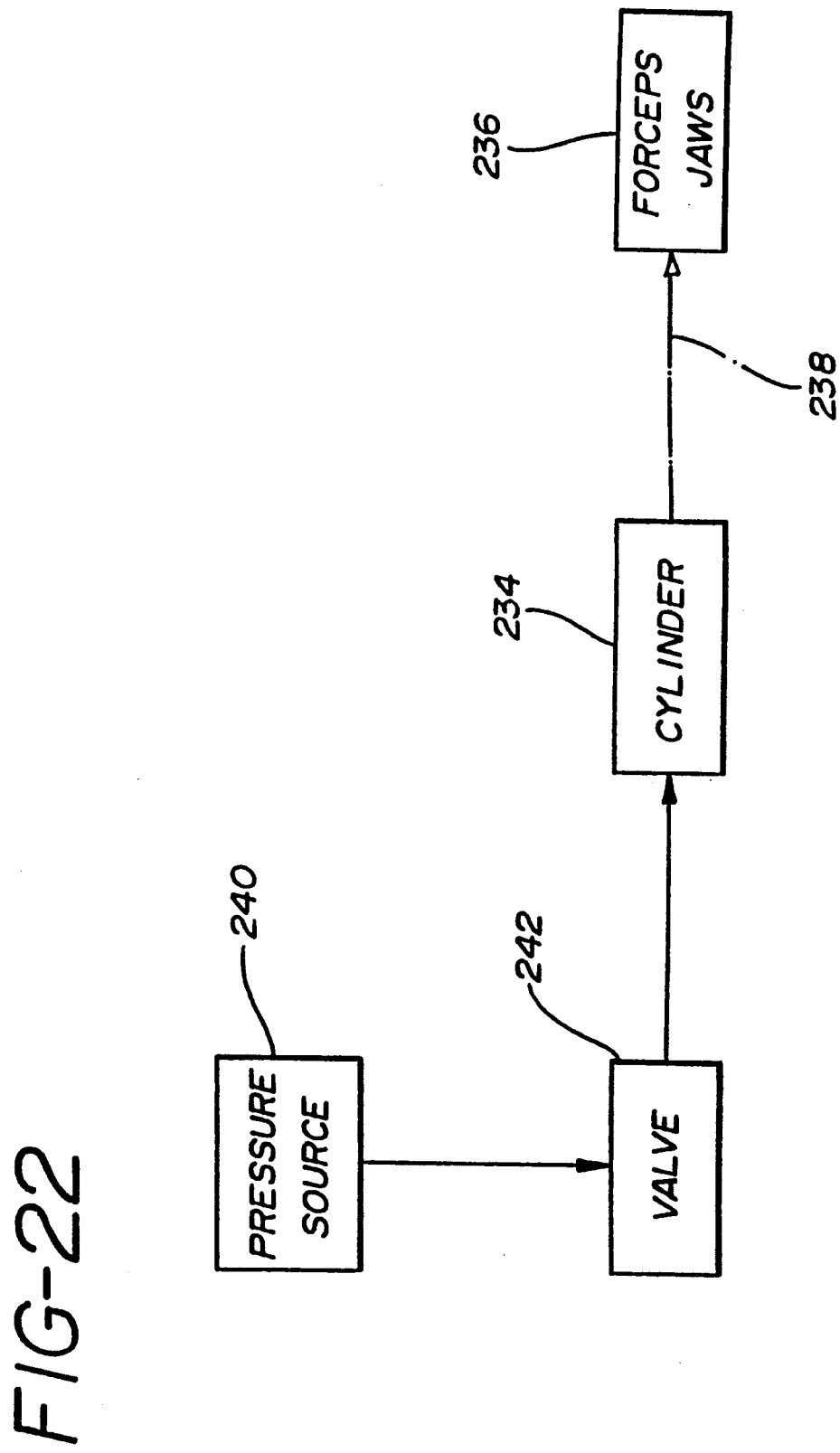

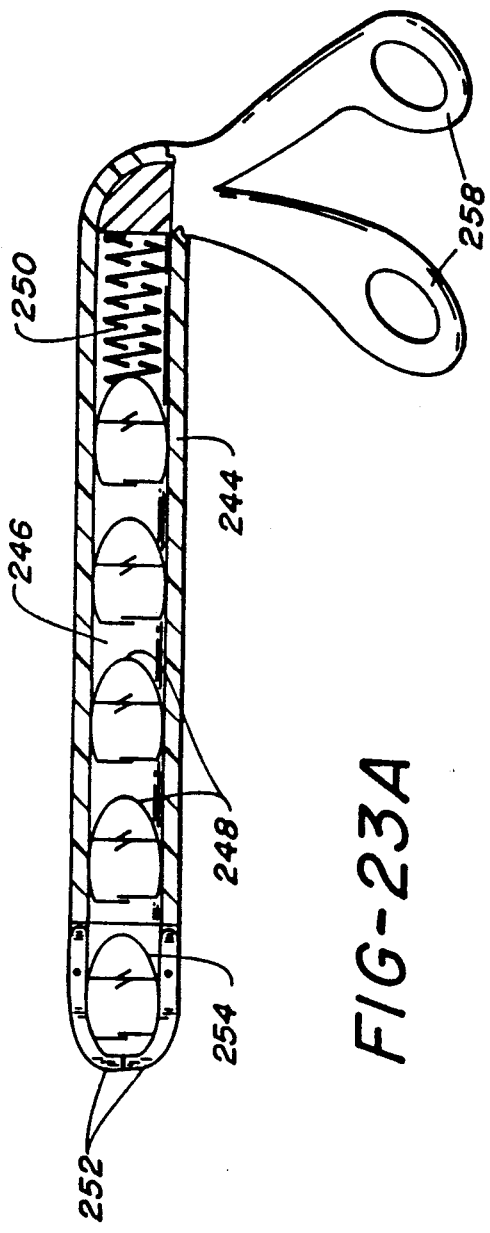
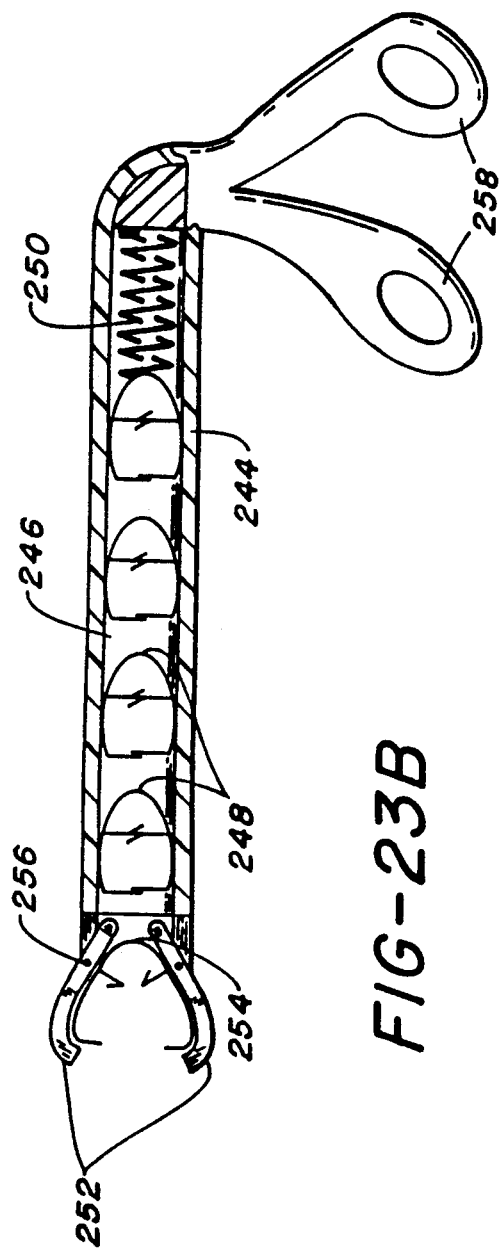
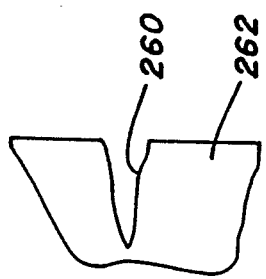
FIG-23A
FIG-23B

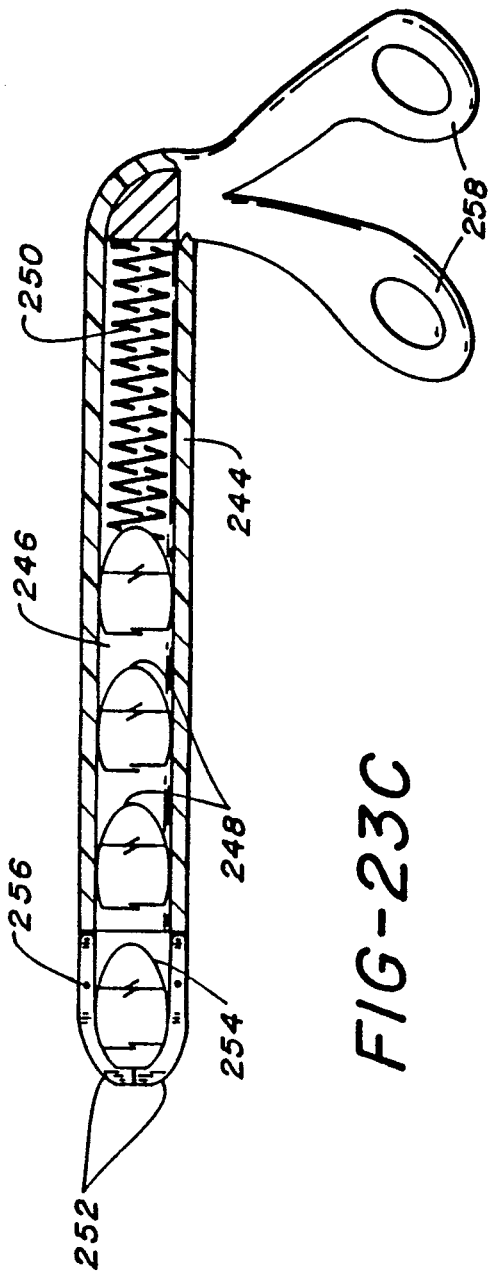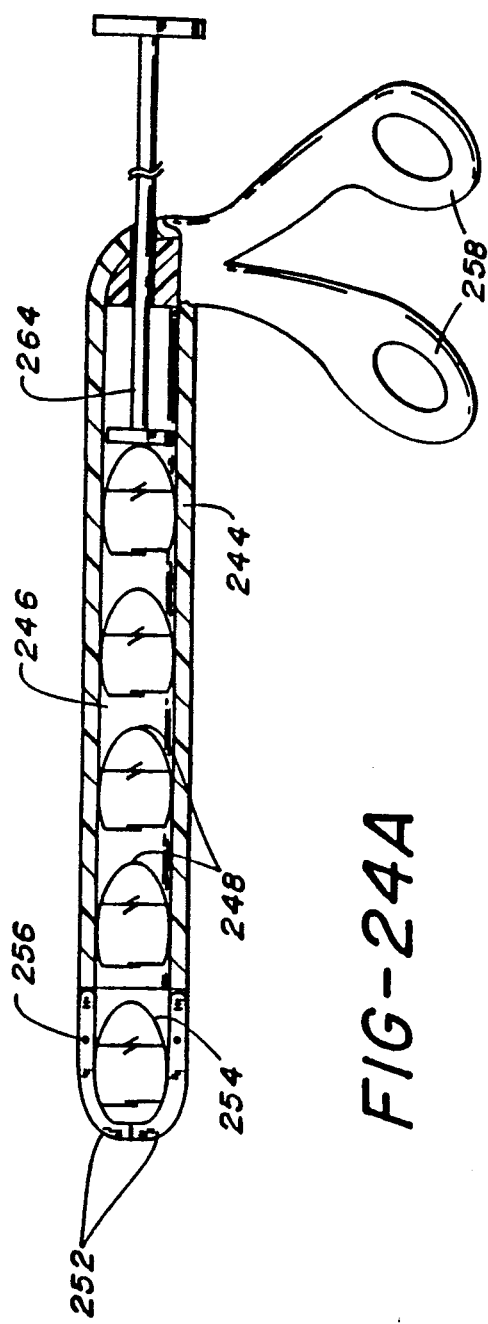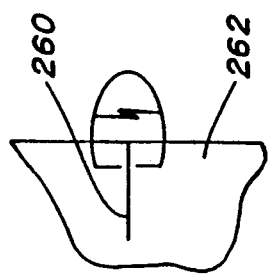
FIG-23C
FIG-24A

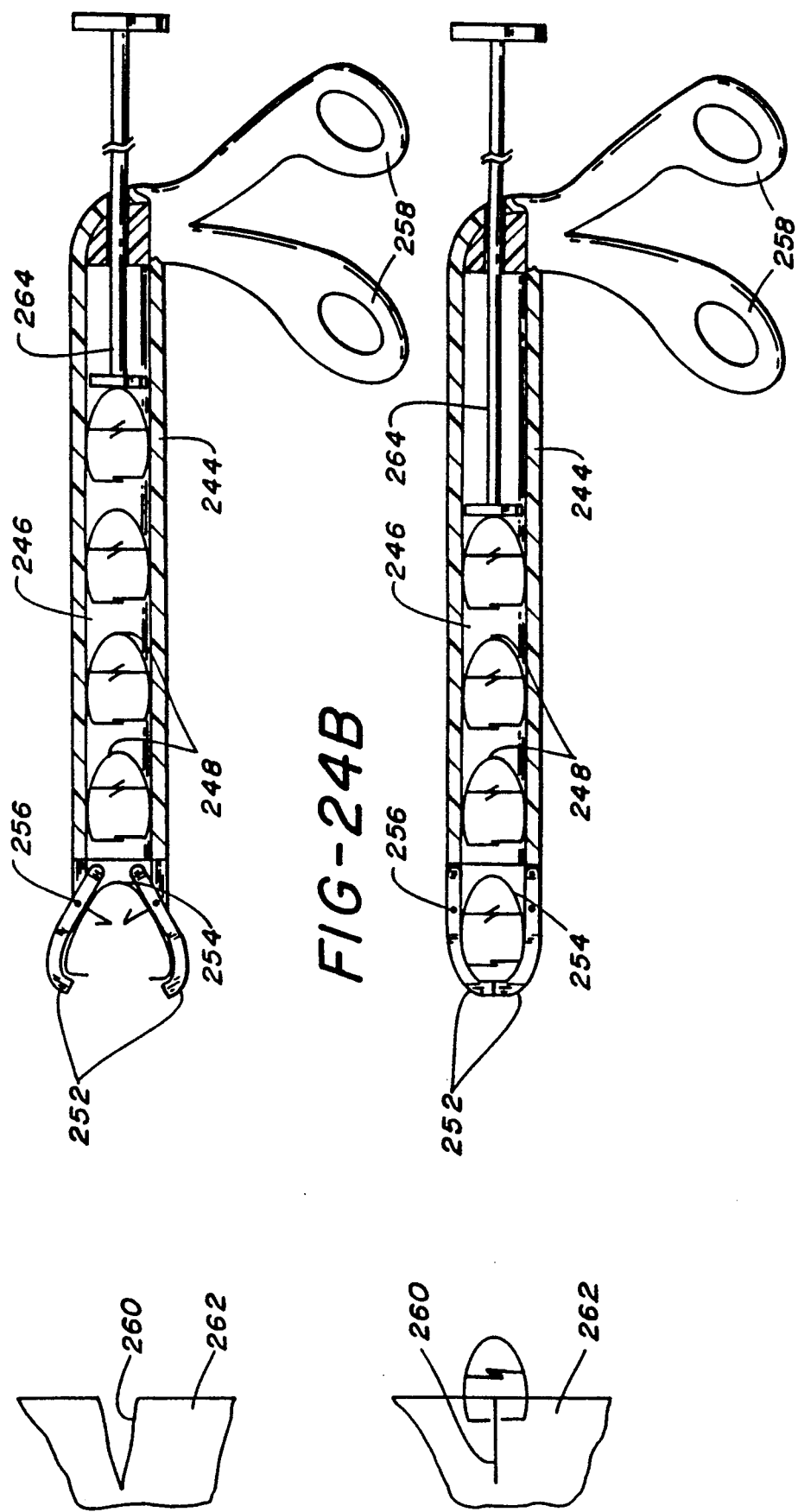

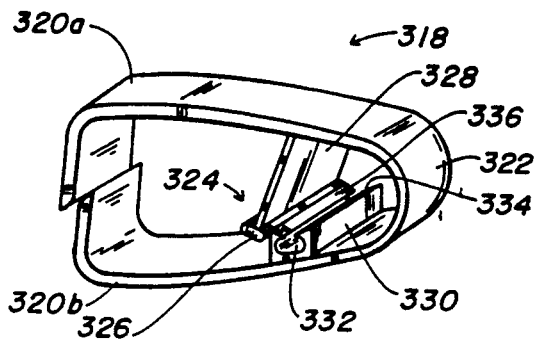
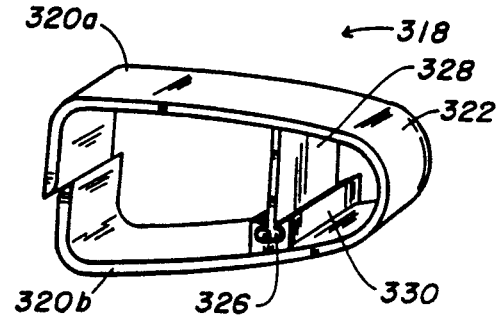
FIG-28A   FIG-28B
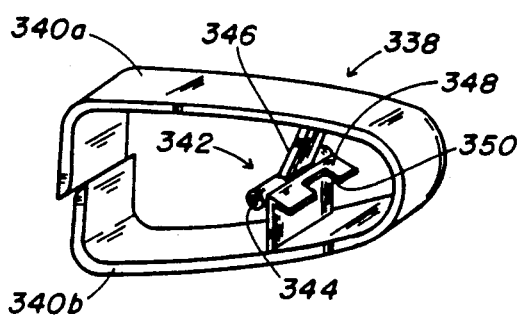
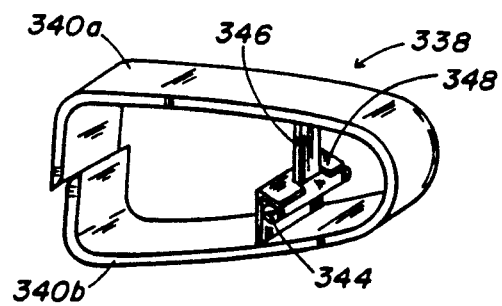
FIG-29A   FIG-29B
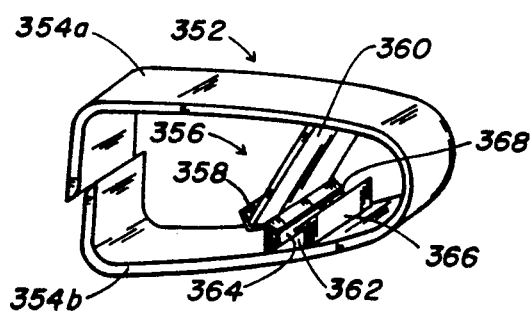
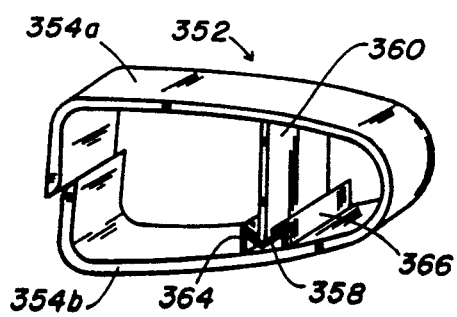
FIG-30A   FIG-30B

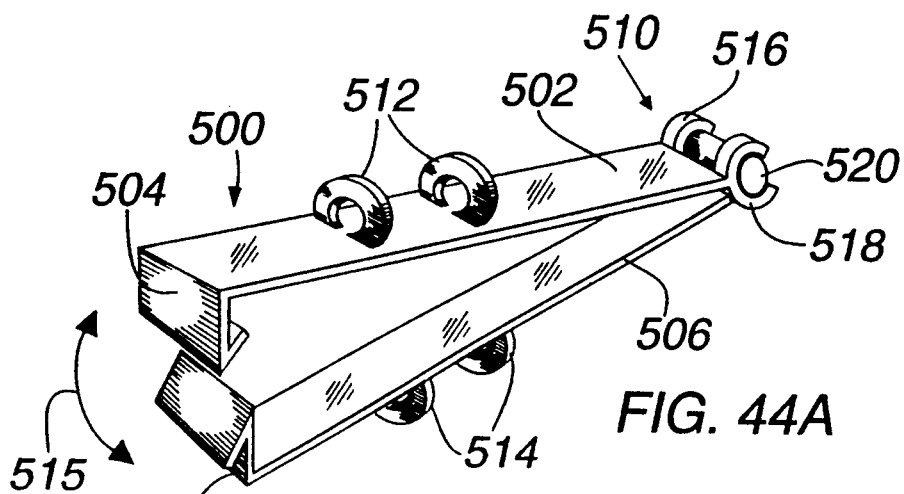
FIG. 44A
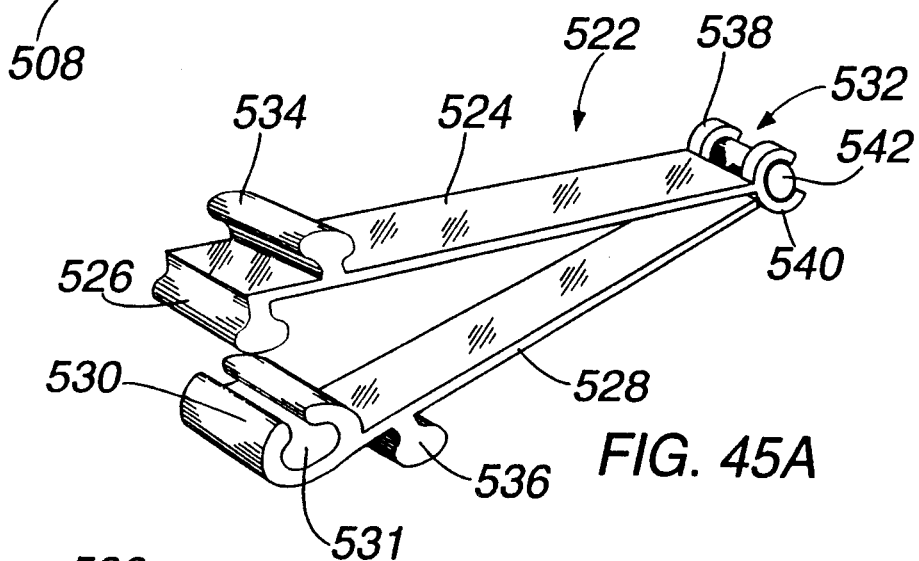
FIG. 45A
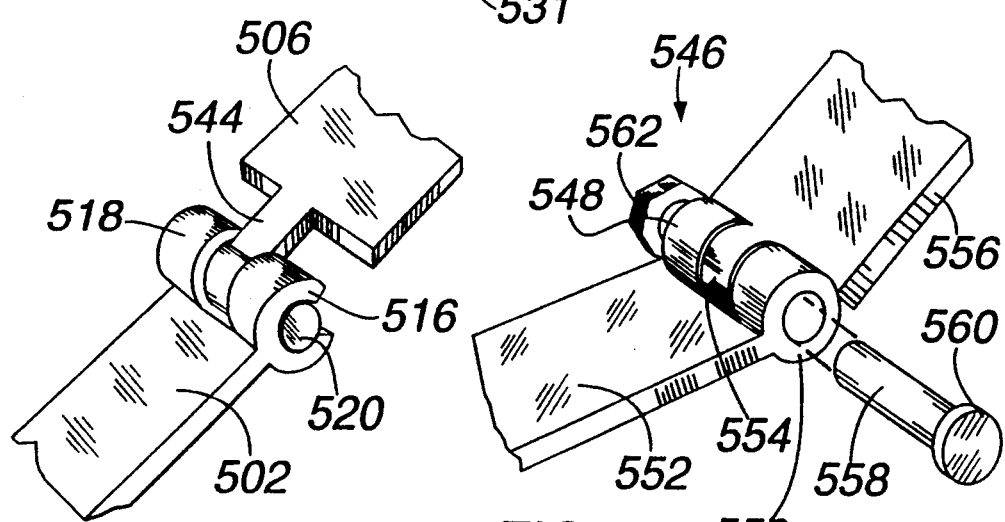
FIG. 46
FIG. 47

ENDOSCOPIC STAPLING DEVICE AND RELATED STAPLE

CROSS-REFERENCE TO RELATED APPLICATIONS

This application is a continuation-in-part of commonly owned U.S. patent application Ser. No. 695,702 filed May 3, 1991 now U.S. Pat. No. 5,156,609, (which is in turn a continuation-in-part of applications Ser. No. 456,960 filed Dec. 28, 1989 and Ser. No. 543,704 filed Jun. 26, 1990, now U.S. Pat. Nos. 5,015,249 and 5,049,153, respectively.

BACKGROUND OF THE INVENTION

This invention relates to an endoscopic or laparoscopic stapling device and to an associated surgical staple. More particularly, this invention relates to a device usable with an endoscope and/or in a laparoscopic surgical procedure for performing a stapling operation on a patient's internal body tissues at a surgical site not visible to the unaided eye.

Conventional surgical techniques for repairing tissue injuries such as hernias and perforated ulcers, for closing other openings in internal body tissues and for ligating tubular body organs such as sperm ducts and Fallopian tubes, generally require that an extensive incision be made in the patient's abdominal wall. Such an operation is generally traumatic to the patient, involves considerable surgeon time and requires a relatively lengthy convalescence. This is the case even though only one or a small number of sutures is required to repair the injury or tie off the vessel.

U.S. Pat. Nos. 5,015,249 and 5,049,153 disclose a method for stapling internal body tissues wherein a staple is provided having a spring bias tending to force the staple into an opened configuration. The staple has a pair of legs connected to one another by a bight portion and further has an additional spring bias or a pair of locking elements for maintaining the staple in a closed postfiring configuration. The method in accordance with disclosures of U.S. Pat. Nos. 5,015,249 and 5,049,153 comprises the steps of (a) exerting a closure force on the staple to hold the staple in a closed prefiring configuration inside the distal end of a surgical instrument in opposition to the spring bias, (b) shifting the staple in a distal direction to eject the staple from the surgical instrument, (c) relaxing the closure force, thereby permitting the staple to open under the spring bias, (d) inserting distal ends of the legs into the internal body tissues to be stapled, and (e) closing the staple and maintaining the staple in the closed postfiring configuration.

Endoscopic or laparoscopic surgical procedures utilizing the stapling closure operation of U.S. Pat. Nos. 5,015,249 and 5,049,153 represent a significant advance in operative techniques. However, the surgical staple with the spring bias is difficult to manufacture and is possibly unwieldy and difficult to control in surgery. Accordingly, a surgical staple and an associated staple assembly are needed which will simplify manufacture and facilitate implementation of the endoscopic/laparoscopic stapling techniques of the afore-mentioned patents.

OBJECTS OF THE INVENTION

An object of the present invention is to provide a surgical staple assembly for use with endoscopes and/or in laparoscopic surgical procedures to close openings internal to a patient's body.

Another object of the present invention is to provide an associated staple for use with endoscopes and/or in laparoscopic surgical procedures to close openings internal to a patient's body.

A more particular object of the present invention is to provide such a surgical stapling assembly and associated staple which are easy to manufacture and to control in operation.

SUMMARY OF THE INVENTION

A surgical staple, particularly but not exclusively for use in endoscopic or laparoscopic surgery comprises, in accordance with the present invention, a first leg provided with a first locking element, a second leg provided with a second locking element, and a hinge joining the first leg and the second leg to one another. The first locking element and the second locking element are designed to cooperate with one another to maintain the staple in a closed postfiring configuration. The staple is disposed in a closed prefiring configuration wherein at least one of the first leg, the second leg, the first locking element and the second locking element is deformed to prevent cooperation of the first locking element and the second locking element.

Pursuant to another feature of the present invention, the first leg and the second leg are provided with elements which enable a pivoting of the legs away from one another and about the hinge during a staple opening operation. Such elements may include loop-shaped elements or eyelets, or snap-lock projections such as knobs or cooperating snap-lock-type recesses.

According to another feature of the present invention, the hinge is a rotary type hinge essentially free of internal stresses. More specifically, the hinge includes a sleeve-type element on one of the staple legs and a pin type element on the other leg, the pin being inserted at least partially into the sleeve.

Pursuant to an additional feature of the present invention, a tubular member surrounding the staple is provided for maintaining the staple in the closed prefiring configuration.

The locking elements on the staple legs may be disposed proximately to the hinge (at a proximal end of the staple). Alternatively, the staple locking elements are disposed at ends of the first leg and the second leg opposite the hinge.

A surgical staple assembly comprises, in accordance with another embodiment of the present invention, a staple including (i) a first leg provided with a first locking element, (ii) a second leg provided with a second locking element, and (iii) a hinge including cooperating elements on the first leg and the second leg for pivotably joining the first leg and the second leg to one another. The first locking element and the second locking element are adapted to cooperate with one another to maintain the staple in a closed postfiring configuration. In addition, means are provided for maintaining the staple in a closed prefiring configuration wherein the first leg and the second leg are staggered with respect to one another so that the first locking element and the second locking element are spaced from one another to prevent interlocking thereof and wherein the cooperating hinge elements are spaced from one another.

As discussed above, the staple is maintained in the closed prefiring configuration by a tubular member in which the staple is disposed.

Pursuant to another feature of the present invention, the staple legs are provided with locking elements for enabling the legs to be moved away from one another during a staple opening operation.

The cooperating hinge elements may take the form of a slotted sleeve-type element on one staple leg and a pin type element on the other staple leg, the pin being insertable at least partially into the sleeve.

A surgical staple assembly comprises, in accordance with a further embodiment of the present invention, a staple including a first leg portion provided with a pair of spaced first locking elements and a second leg portion provided with a pair of spaced second locking elements. The first locking elements and the second locking elements are adapted to cooperate with one another to maintain the staple in a closed postfiring configuration. Moreover, means are provided for maintaining the staple in a prefiring configuration wherein the first leg portion and the second leg portion are spaced with respect to one another to prevent interlocking of the first locking elements and the second locking elements.

As discussed above, the staple is maintained in the closed prefiring configuration by a tubular member in which the staple is disposed.

The staple in accordance with this embodiment of the invention further includes means on the staple legs for enabling the legs to be moved away from one another during a staple opening operation.

Pursuant to another feature of the present invention, the first locking elements are disposed proximately to each other and to one end of the first leg portion, while the second locking elements are disposed proximately to each other and to one end of the second leg portion. Alternatively, the first and second locking elements are each disposed at opposite ends of the respective staple legs.

A surgical device utilizable with an endoscope or rigid tubular member for performing an endoscopic or laparoscopic stapling operation comprises, in accordance with the present invention, (a) a forceps member slidably disposable inside a biopsy channel of an endoscopic or laparoscopic instrument, (b) an actuator element operatively connected to the forceps member for manipulating jaws of the forceps member between opened and closed positions, and (c) a staple having a pair of legs and a hinge joint for coupling the legs at one end to one another so that the legs swing substantially freely about the joint. The staple legs are provided with respective locking elements which cooperate with one another to maintain the staple in a closed postfiring configuration. Also, the staple is disposed in the prefiring configuration between the jaws when the jaws are closed. The surgical device further comprises locking components on the legs and the jaws for temporarily locking the legs to the jaws at least during an opening motion of the jaws, whereby the legs are pivoted about the hinge joint to open the staple from the prefiring configuration.

Pursuant to another feature of the present invention, the locking components includes longitudinally slidable rods on the forceps member and aperture forming elements on the staple legs. Alternatively, the locking components include snap-lock-type projections and cooperating recesses.

In an additional feature of the surgical device, at least one of the legs and the locking elements is deformed in the prefiring configuration of the staple to prevent cooperation of the locking elements. Alternatively, the staple legs are staggered with respect to one another in the prefiring configuration of the staple to prevent cooperation of the locking elements.

Another surgical device utilizable with an endoscope or rigid tubular member for performing an endoscopic or laparoscopic stapling operation comprise, in accordance with the present invention, (a) a forceps member slidably disposable inside a biopsy channel of an endoscopic or laparoscopic instrument, (b) an actuator element operatively connected to the forceps member for manipulating jaws of the forceps member between opened and closed positions, and (c) a surgical staple including a first leg portion provided with a pair of spaced first locking elements and a second leg portion provided with a pair of spaced second locking elements, the first locking elements and the second locking elements being adapted to cooperate with one another to maintain the staple in a closed postfiring configuration. The surgical device further comprises locking components on the staple legs and the forceps jaws for temporarily locking the staple legs to respective ones of the jaws at least during an opening motion of the jaws, whereby the legs are moved away from one another prior to completion of a staple firing operation.

A surgical staple and an associated staple assembly in accordance with the present invention simplify manufacture and facilitate implementation of the endoscopic/laparoscopic stapling techniques.

BRIEF DESCRIPTION OF THE DRAWING

FIGS. 4A–4I are partially schematic, partial perspective views, taken from the side and on a reduced scale, of an endoscopic stapling device, showing successive stages in the application of a surgical staple to internal body tissues.

FIGS. 8A–8F are partially schematic, partial perspective views, similar to FIGS. 8A–8F, of another endoscopic stapling device, showing successive stages in the application of the surgical staple of FIGS. 5 and 6 to internal body tissues.

FIG. 16 is a partial longitudinal cross-sectional view of another endoscopic stapling device, showing a forceps member and a staple in a closed prefiring configuration between jaws of the forceps member.

FIG. 17 is a partial longitudinal cross-sectional view of the endoscopic stapling device of FIG. 16, showing the forceps member in an extended position relative to a tubular sheath.

FIG. 18 is a partial longitudinal cross-sectional view of the endoscopic stapling device of FIGS. 16 and 17, showing the forceps member and the staple in an opened configuration.

FIG. 19 is a top view of the forceps member of FIGS. 16, 17 and 18.

FIGS. 20A through 20D are schematic partial side elevation views showing successive steps in the operation of an endoscopic stapling device like the device of FIGS. 16-19.

FIG. 22 is a block diagram of yet another endoscopic stapling device.

FIGS. 23A-23C are schematic diagrams showing successive stages in the operation of an endoscopic or laparoscopic staple applicator with a staple magazine.

FIGS. 24A-24C are schematic diagrams showing successive stages in the operation of another endoscopic or laparoscopic staple applicator with a staple magazine.

FIGS. 28A and 28B are side perspective views of a further staple or clip, showing the staple in a closed prefiring and a closed postfiring configuration, respectively.

FIGS. 29A and 29B are side perspective views of an additional staple or clip, showing the staple in a closed prefiring and a closed postfiring configuration, respectively.

FIGS. 30A and 30B are side perspective views of another staple or clip, showing the staple in a closed prefiring and a closed postfiring configuration, respectively.

FIGS. 31A, 31B and 31C are side perspective views of yet another staple or clip, showing the staple in a closed prefiring, a first closed postfiring configuration and a second closed postfiring configuration, respectively.

FIG. 44A is a schematic side perspective view, on an enlarged scale, of a surgical staple in accordance with the present invention, for use in endoscopic and/or laparoscopic procedures.

FIG. 45A is a schematic side perspective view, also on an enlarged scale, of another surgical staple in accordance with the present invention, for use in endoscopic and/or laparoscopic procedures.

FIG. 46 is a partial perspective view, on an even larger scale, of a hinge assembly or joint in the staple of FIG. 44 or FIG. 45.

FIG. 47 is a partial perspective view, on an enlarged scale, of an alternative hinge assembly or joint for the staple of FIG. 44 or FIG. 45.

DETAILED DESCRIPTION

Figure 1:
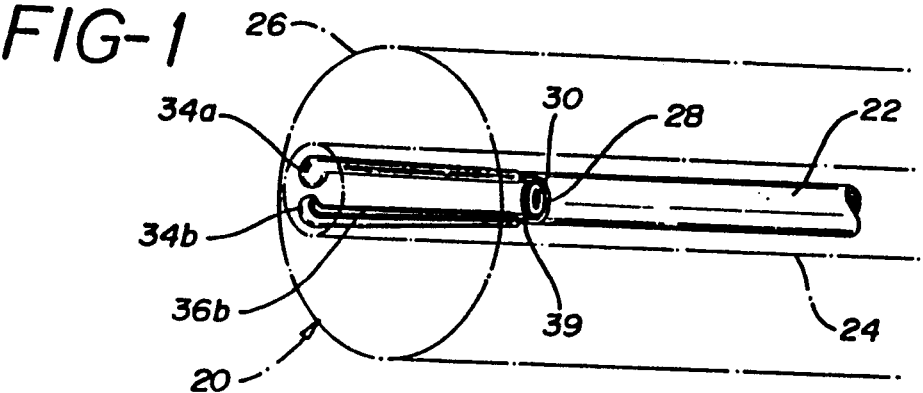
FIG. 1 is a partial perspective view, taken from the side, of an endoscopic stapling device in a prefiring configuration without a loaded staple.
Figure 2:
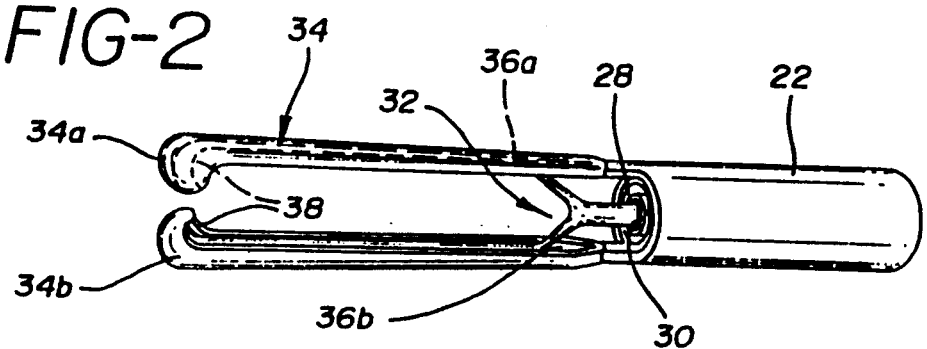
FIG. 2 is a partial perspective view, similar to FIG. 1, showing the endoscopic stapling device in the prefiring configuration with a loaded staple in a closed configuration.

As illustrated in FIGS. 1 and 2, an endoscopic stapling device 20 comprises an outer elongate flexible tubular member 22 having a diameter sufficiently small so that the tubular member is slidably insertable into a biopsy channel 24 extending longitudinally through a flexible tubular endoscope member 26. Endoscopic stapling device 20 further comprises an inner elongate flexible tubular member 28 slidably disposed inside tubular member 22 and an elongate flexible rod member 30 slidably disposed inside inner tubular member 28. In the prefiring configuration of FIG. 2, a staple 32 is disposed in a closed configuration at least partially inside inner tubular member 28 distally of a distal end of rod member 30.

Figure 3:
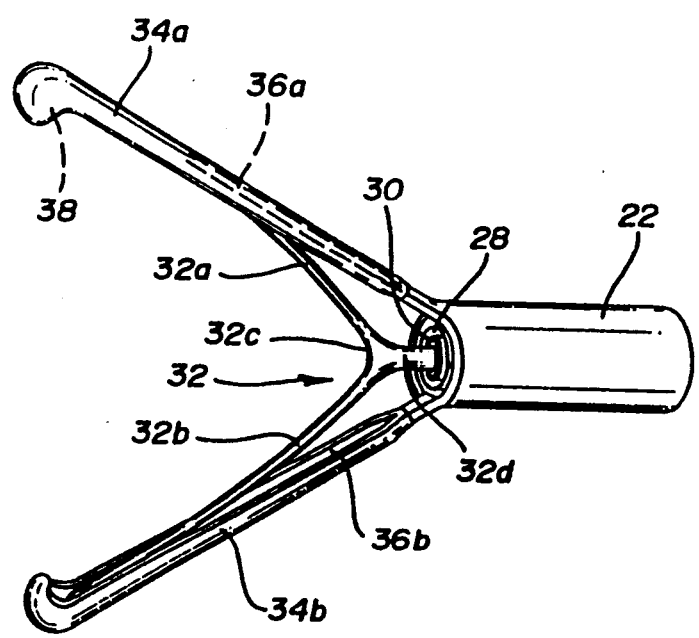
FIG. 3 is a partial perspective view, taken from the side, of the endoscopic stapling device of FIGS. 1 and 2, showing the device in an initial firing stage with an opened staple.

Outer tubular member 22 is provided at a distal end with a forceps 34 including a pair of spring loaded jaws 34a and 34b. As shown in FIGS. 2 and 3, staple 32 includes a pair of legs 32a and 32b seated in the prefiring configuration of the endoscopic stapling device 20 in grooves 36a and 36b provided on inwardly facing surfaces of forceps jaws 34a and 34b. As described hereinafter with reference to FIGS. 4A-4I, jaws 34a and 34b serve to open staple 32 upon an ejection thereof from inner tubular member 28 by a distally directed motion of rod member 30. Jaws 34a and 34b are releasably connected to staple legs 32a and 32b so that staple 32 becomes detached from forceps 34 upon the attainment of a predetermined angular displacement between jaws 34a and 34b. More particularly, the free ends of staple legs 32a and 32b are held in the prefiring configuration of the endoscopic stapling device in cup-shaped recesses 38 formed at the free ends of jaws 34a and 34b.

Staple 32 further includes a bight portion 32c joining staple legs 32a and 32b to one another and to a planar projection 32d extending away from bight portion 32c in a direction opposite legs 32a and 32b. In the staple loaded configuration of FIG. 2, projection 32d is received in a cross-sectionally rectangular recess or opening 39 at the distal end of rod member 30.

It is to be noted that projection 32d and recess 39 may have any of several different geometric shapes. In particular, other polygonal cross-sections can be used.

As shown in FIGS. 4A through 4I, endoscopic stapling device 20 includes an assembly 40 at its proximal end for enabling the operation of the device by a surgeon during an operation. Assembly 40 includes a housing or casing member 42 mountable to endoscope 26 at a proximal end thereof. Projecting from casing 42 are a plurality of handles or knobs 44, 46 and 48 which are mechanically connected to outer tubular member 22, rod member 30 and inner tubular member 28, respectively, for enabling the sliding of those members along biopsy channel 24 by a surgeon or other authorized operator. FIGS. 4A through 4I show the positions of handles 44, 46 and 48 corresponding to the operative configurations of outer tubular member 22, rod member 30, inner tubular member 28, and staple 32 shown in the respective drawing figures.

Figure 4A:
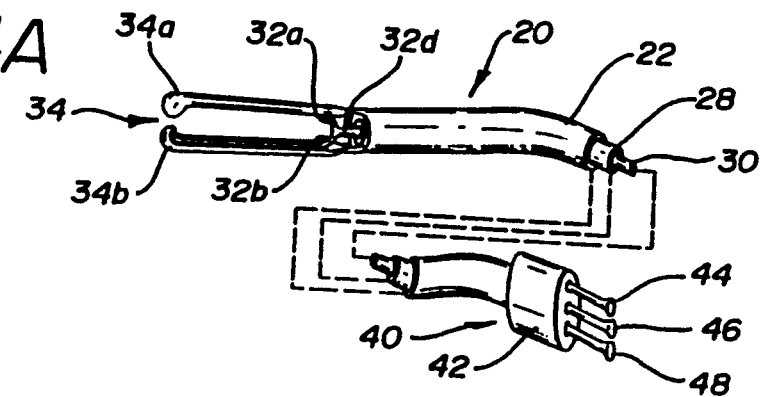
Figure 4B:
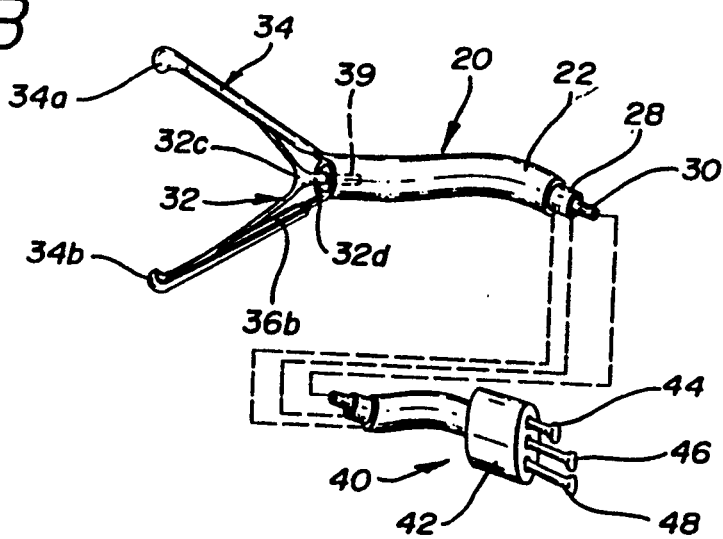

FIGS. 4A and 4B are similar to FIGS. 2 and 3. FIG. 4A shows endoscopic stapling device 20 in a prefiring configuration in which outer tubular member 22, inner tubular member 28, rod 30 and staple 32 are all located in biopsy channel 24 of endoscope 26. More specifically, staple 32 is disposed in a closed prefiring configuration distally of rod member 30 and inside tubular member 28 at the distal end thereof. Endoscope 26 has already been inserted through an aperture (not illustrated) in a patient's body (not shown) and has been used to visually locate in the patient's body the internal body tissues upon which a stapling operation is to be performed. The internal body tissues may be a vessel or duct which needs to be closed or perhaps an opening in the stomach wall.

Figure 4C:
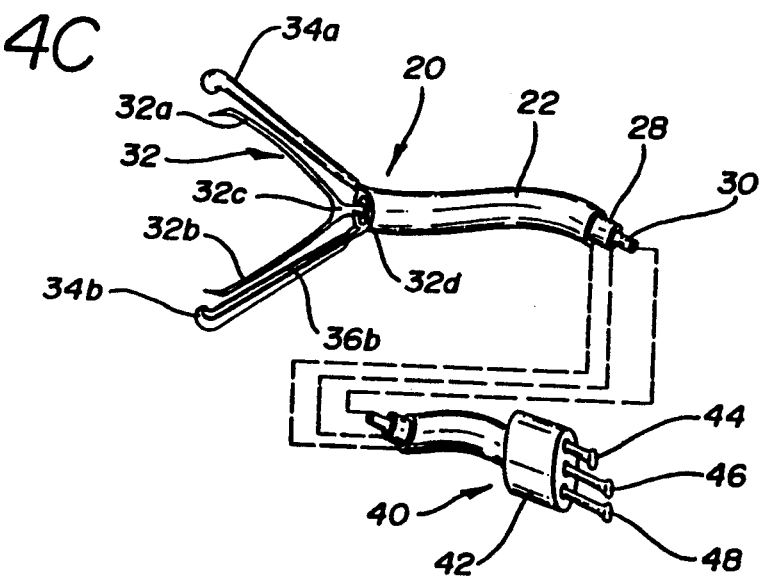

Upon the locating of the surgical site, tubular outer member 22 and rod member 30 are pushed in the distal direction through biopsy channel 24 to eject staple 32 from tubular member 28. During this distal motion, jaws 34a and 34b pivot away from one another and pull apart staple legs 32a and 32b, as shown in FIG. 4B. Upon a further outward pivoting of jaws 34a and 34b, the free ends of legs 32a and 32b slip out from recesses 38 at the distal ends of grooves 36a and 36b. Staple 32 is now in a released, opened configuration, as depicted in FIG. 4C.

Figure 4D:
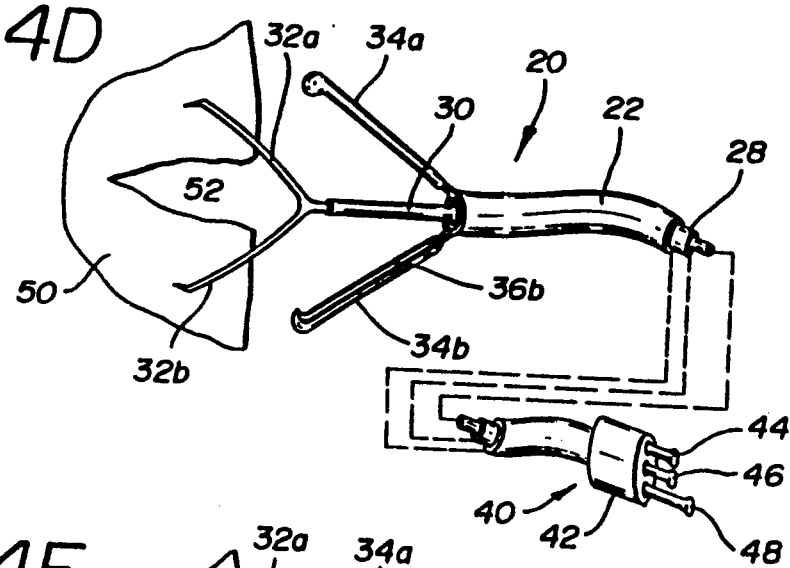

In the next step of a surgical procedure using endoscopic stapling device 20, rod member 30 is pushed further in the distal direction to move opened staple 32 towards internal body tissues 50 having an opening 52 previously detected through the optical pathway (not illustrated) of endoscope 26. FIG. 4D shows staple 32 substantially embedded in the body tissues 50 in a region about opening 52.

Upon the embedding of opened staple 32 in internal body tissues 50, inner tubular member 28 is pushed in the distal direction to engage staple legs 32a and 32b and thereby close the staple about opening 52. The distal motion of inner tubular member 28 relative to rod member 30 and staple 32 bends legs 32a and 32b about bight portion 32c, causing staple 32 to assume a closed, tissue-clamping configuration shown in FIG. 4E.

Figure 4E:
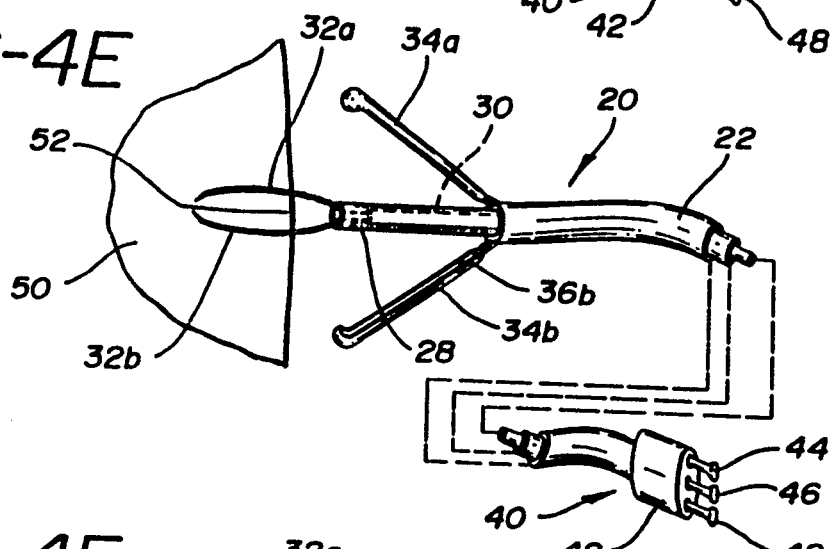
Figure 4F:
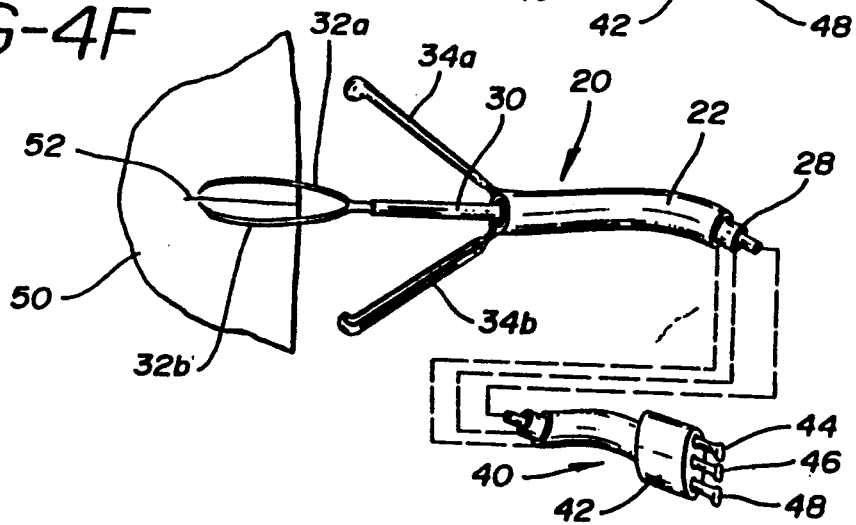

In a subsequent step shown in FIG. 4F, inner tubular member 28 is retracted into biopsy channel 24. In an optional step depicted in FIG. 4G, rod member 30 may be moved even further in the distal direction to push staple 32 further into tissues 50. This step serves to limit the extent that the staple projects from tissues 50.

Upon a satisfactory disposition of staple 32 in tissues 50, whereby opening 52 is stapled closed, rod member 30 is retracted into inner tubular member 28 (FIG. 4H). Outer tubular member 22 is then moved in the proximal direction into biopsy channel 24, jaws 34a and 34b being pivoted towards one another during the proximally directed stroke of outer tubular member 22. The pivoting of jaws 34a and 34b is effectuated by a camming action when the jaws slide past the rim or lip at the distal end of biopsy channel 24.

Upon the completion of the stapling operation, outer tubular member 22, inner tubular member 28 and rod member 30 are all disposed in biopsy channel 24, so that the distal ends of those members do not extend beyond the distal end of the channel. The entire endoscopic instrument is then withdrawn from the patient's body through the aperture through which it was introduced. That aperture may take the form of a natural body opening. Alternatively, the endoscope introduction aperture may be formed through the use of a trocar. Such a procedure can be followed, for example, to repair a hernia through a small opening in the abdominal wall.

Figure 5:
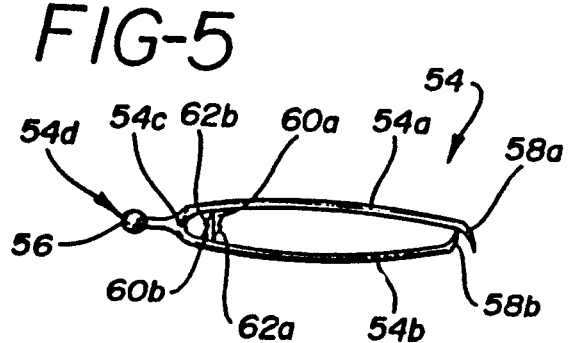
FIG. 5 is a side elevational view, on an enlarged scale, of a staple for use in an endoscopic stapling device, showing the staple in a prefiring closed configuration.
Figure 6:
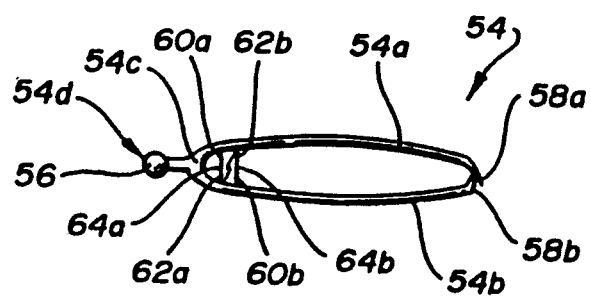
FIG. 6 is a side elevational view of the staple of FIG. 5, showing the staple in a closed, postfiring configuration.

As illustrated in FIGS. 5 and 6, a staple 54 for an endoscopic stapling device includes a pair of legs 54a and 54b joined by a bight section 54c and provided on a side of the bight section opposite the legs with a projection 54d terminating in a knob or ball 56. Each leg 54a and 54b is provided at a free end with a respective inwardly turned foot 58a and 58b. In addition, on their inwardly facing sides, legs 54a and 54b are provided towards the proximal end of the staple with interlocking finger elements 60a and 60b having barbs or hooks 62a and 62b which cooperate with one another to lock the staple in a closed configuration at the end of a stapling operation.

Staple 54 is spring biased, by virtue of the inherent structural characteristics of its preferably metallic material, towards an opened (legs spread) configuration. The material and dimensions of staple 54 are selected so that the staple is sufficiently flexible to be temporarily distorted into the prefiring configuration shown in FIG. 5. In that configuration, legs 54a and 54b are longitudinally shifted relative to one another and interlocking finger elements 60a and 60b releasably engage each other along planar faces 64a and 64b.

Figure 7A:
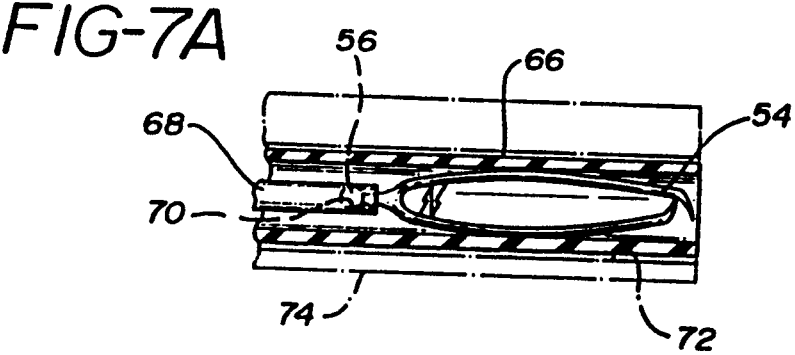
FIGS. 7A–7F are partially schematic, partial perspective views, taken from the side and on a reduced scale, of an endoscopic stapling device, showing successive steps in the application of the surgical staple of FIGS. 5 and 6 to internal body tissues.

As illustrated in FIG. 7A, staple 54 is disposed in its prefiring configuration inside the distal end of an elongate flexible tubular member 66 distally of an elongate flexible rod member 68 itself slidably inserted in tubular member 66. Staple 54 is releasably attached to rod member 68 by a ball and socket connection comprising knob 56 and a corresponding recess 70 at the distal end of rod 68.

Figure 7B:
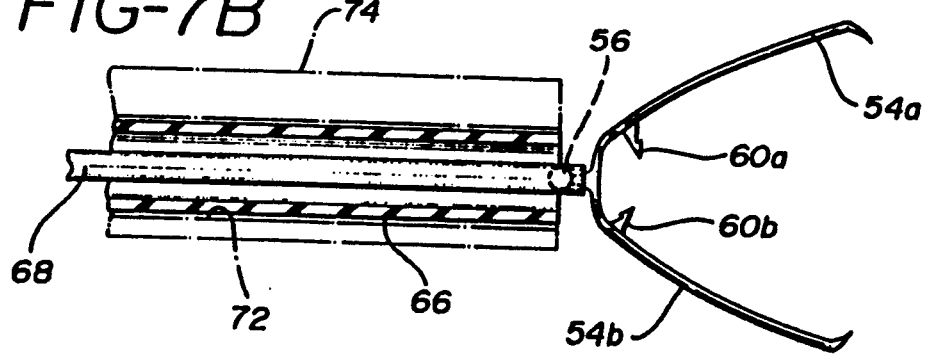
Figure 7C:
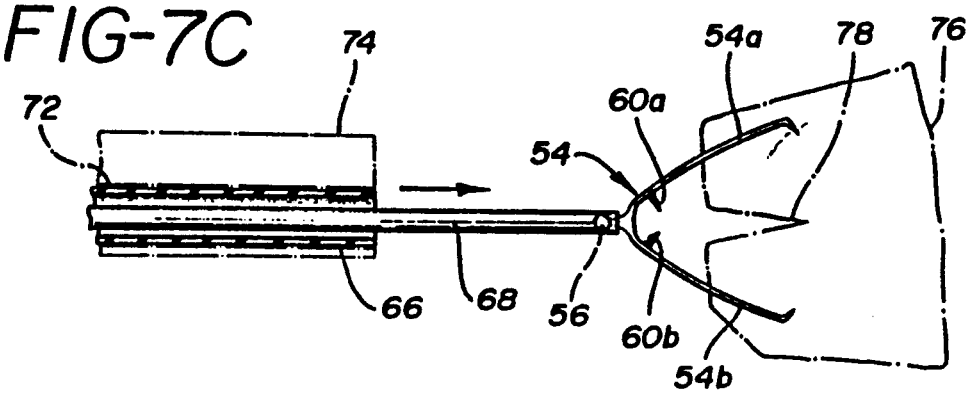

Tubular member 66 has a diameter sufficiently small so that it is slidably insertable into a biopsy channel 72 extending longitudinally through a flexible tubular endoscope member 74. Upon the insertion of the endoscope, with tubular member 66, rod member 68 and staple 54 disposed in the endoscope's biopsy channel, into a patient's body and the location, via the fiberoptics of the endoscope, of an internal site requiring a closure, rod member 68 is shifted in a distal direction to eject staple 54 from tubular member 66. The ejected staple automatically assumes an opened configuration illustrated in FIG. 7B. Further distally directed motion of rod member 68 pushes the opened staple 54 into the internal body tissues 76 of the patient, as shown in FIG. 7C.

Figure 7D:
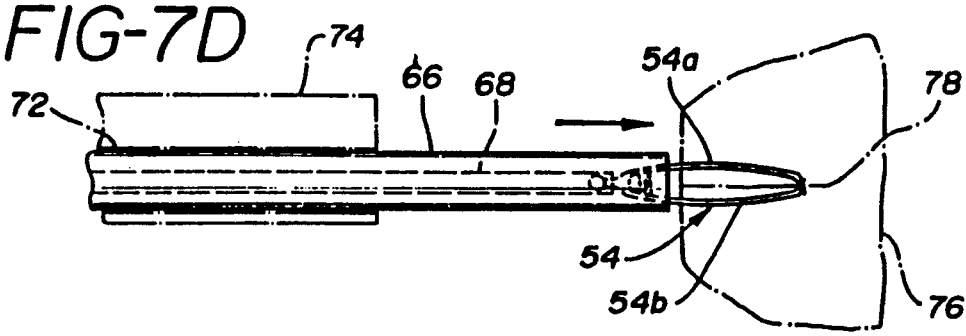
Figure 7E:
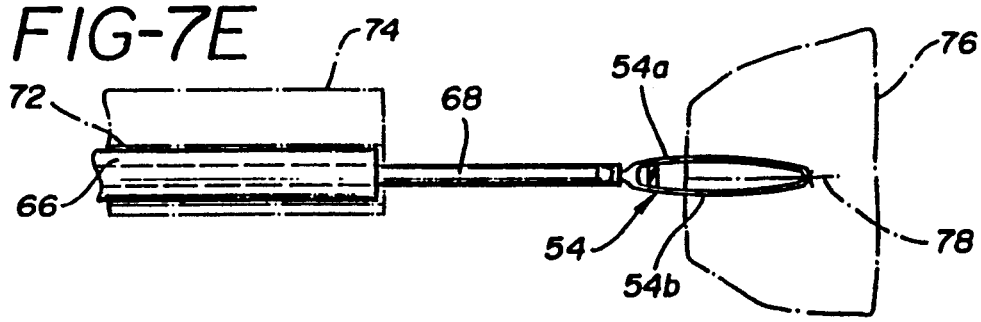
Figure 7F:
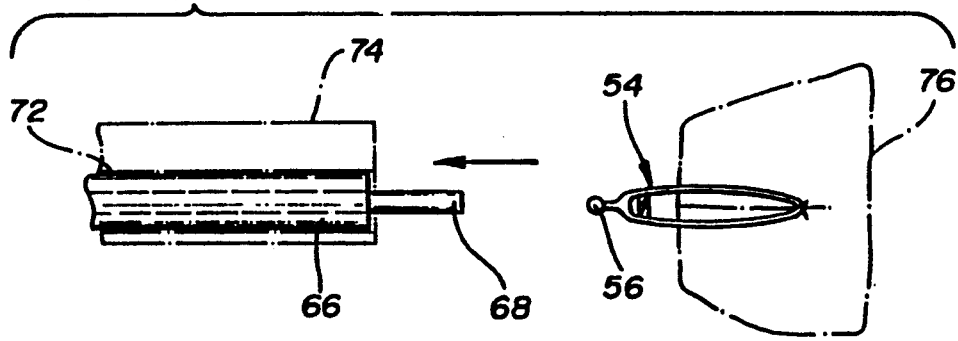

Upon an embedding of staple 54 in body tissues 76 about a cut, tear or other opening 78, tubular member 66 is shifted distally from the endoscope and engages staple legs 54a and 54b to bend them inwardly towards one another in opposition to the internal spring forces of the staple. Upon a sufficient advance of tubular member 66, barbs or hooks 62a and 62b of finger elements 60a and 60b interlock and hold staple legs 54a and 54b in the closed configuration (FIG. 7D). Tubular member 66 is then withdrawn back into the biopsy channel of the endoscope (FIG. 7E). Finally, as depicted in FIG. 7F, rod member 68 is retracted and the endoscope removed from the patient's body.

In an alternative series of steps, rod member 68 is retracted prior to the withdrawal of tubular member 66. In that procedure, tubular member 66 serves to hold staple 54 against the return stroke of rod member 68 and facilitates the removal of knob 56 from recess 70. Usually, however, it is contemplated that the forces holding the ball and socket joint together are smaller than the forces retaining staple 54 in body tissues 76 so that there will be no problem retracting rod member 68 subsequently to the withdrawal of tubular member 66.

As illustrated in FIGS. 8A-8F, another endoscopic stapling device 80 similar to the device of FIGS. 7A-7F includes an outer elongate flexible tubular member 82 having a diameter sufficiently small so that the tubular member is slidably insertable into a biopsy channel 84 extending longitudinally through a flexible tubular endoscope member 86. Endoscopic stapling device 80 further comprises an inner elongate flexible tubular member 88 slidably disposed inside tubular member 82 and an elongate flexible rod member 90 slidably disposed inside inner tubular member 88. In the prefiring configuration of FIG. 8A, a staple 91 (similar to staple 54) is disposed in a closed configuration at least partially inside inner tubular member 88 distally of a distal end of rod member 90. Staple 91 is releasably attached to rod member 90 by a ball and socket connection comprising a knob-like projection 92 on the staple and a corresponding recess 93 at the distal end of rod 90.

Outer tubular member 82 is provided at a distal end with a forceps 94 including a pair of metal jaws 94a and 94b which are spring biased towards a spread-apart state by virtue of their own internal microstructure.

Figures 8A, 8B, 8C:
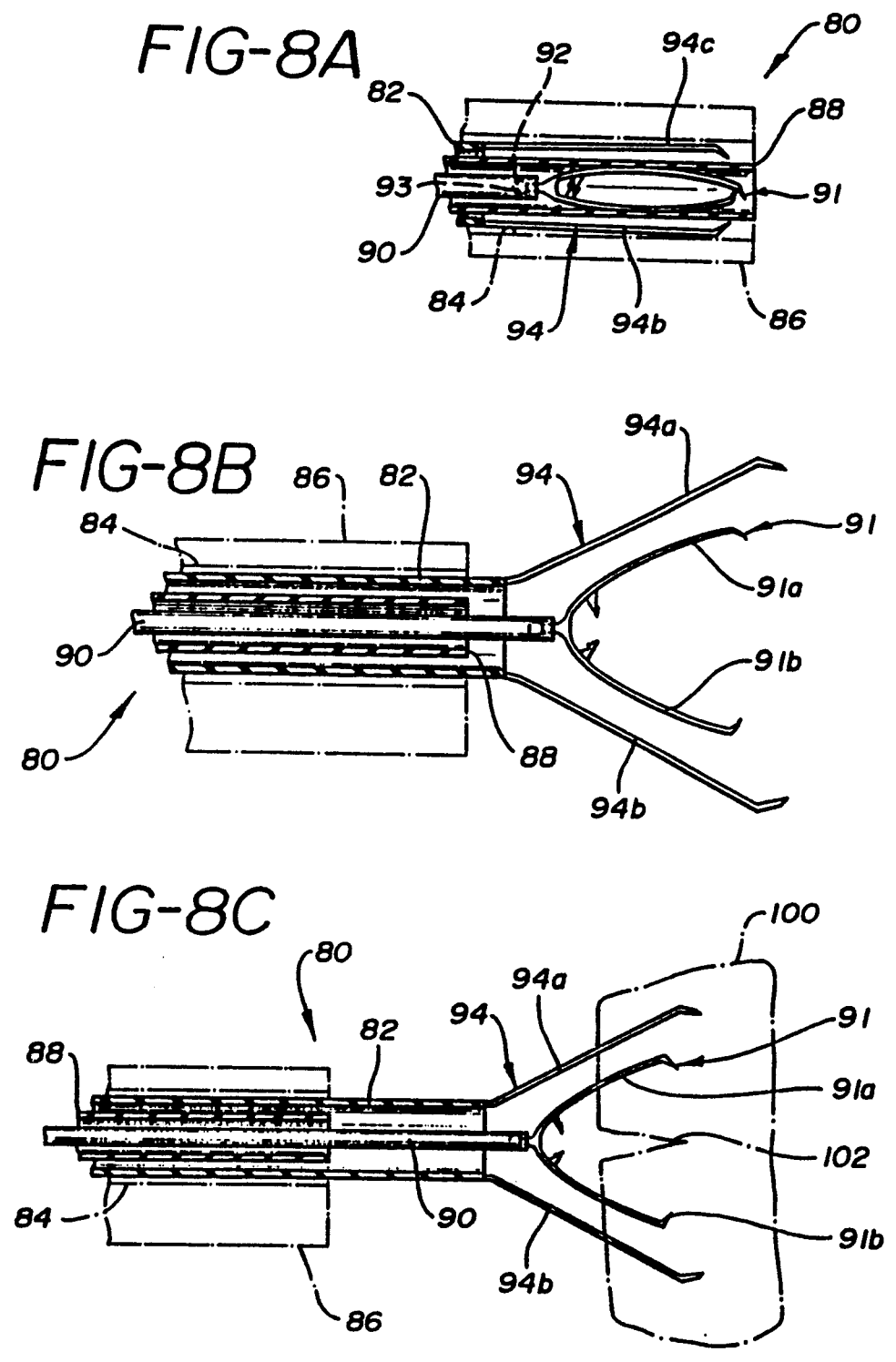

FIG. 8A shows endoscopic stapling device 80 in a prefiring configuration in which outer tubular member 82 including forceps jaws 94a and 94b, inner tubular member 88, rod 90 and staple 91 are all located in biopsy channel 84 of endoscope 86. More specifically, staple 91 is disposed in a closed prefiring configuration (see FIG. 5) distally of rod member 30 and inside tubular member 28 at the distal end thereof.

Endoscope 86 is inserted through an aperture (not illustrated) in a patient's body (not shown) and is used to visually locate in the patient's body the internal body tissues upon which a stapling operation is to be performed. Upon the locating of the surgical site, tubular outer member 82 and rod member 90 are pushed in the distal direction through biopsy channel 84 to open forceps jaws 94a and 94b and to eject staple 91 from tubular member 88, as depicted in FIG. 8B.

In the next step of a surgical procedure using endoscopic stapling device 80, outer tubular member 82 and rod member 90 are pushed further in the distal direction to move opened staple 91 towards internal body tissues 100 having an opening 102 previously detected through the optical pathway (not illustrated) of endoscope 86. FIG. 4C shows forceps jaws 94a and 94b and staple 91 substantially embedded in the body tissues 100 in a region about opening 102.

Figure 8D:
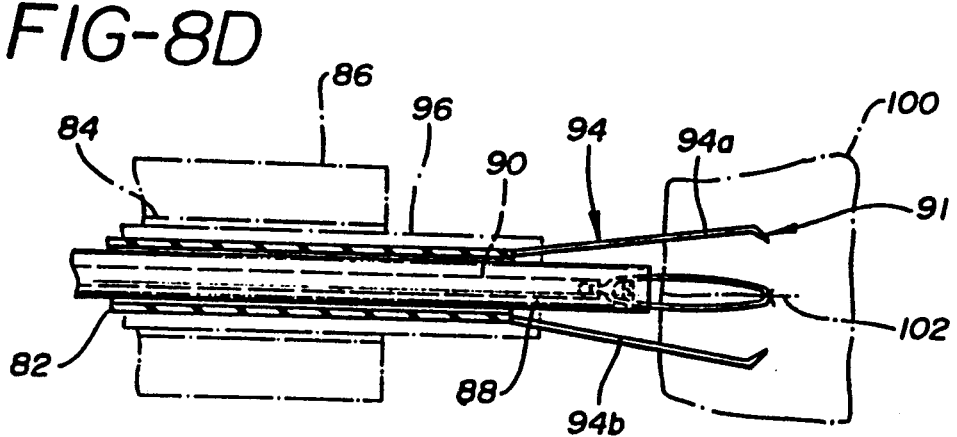
Figure 8E:
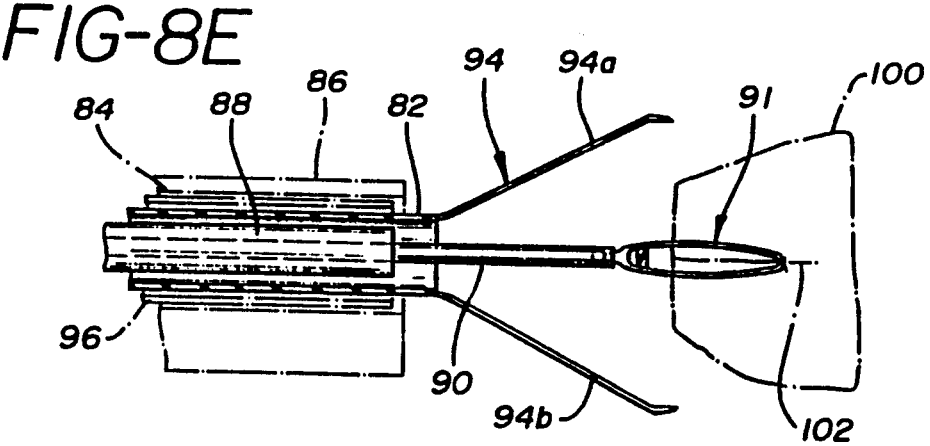
Figure 8F:
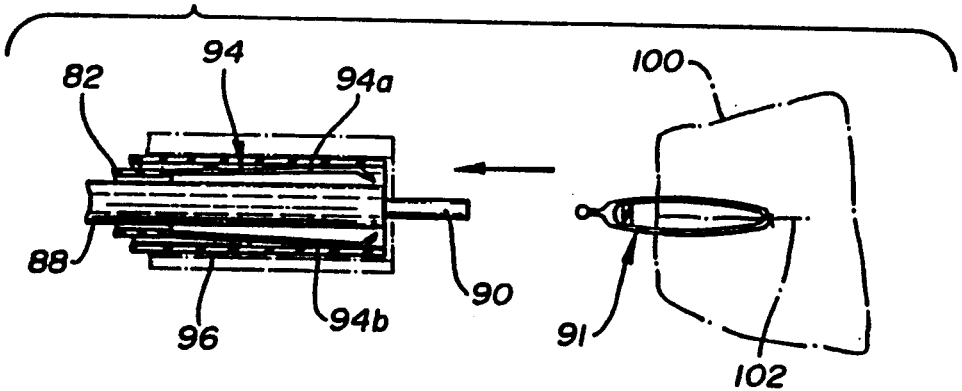
Figure 9:
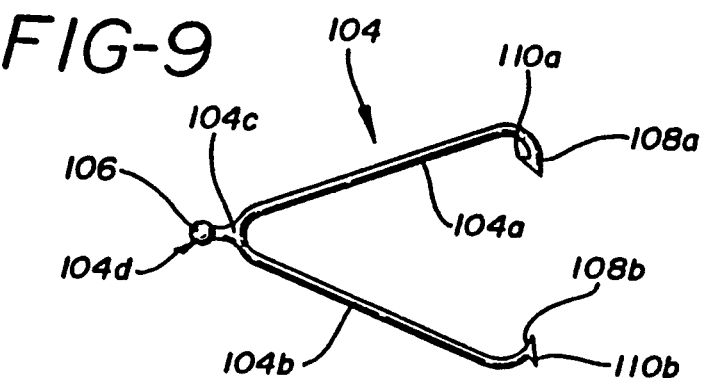
FIG. 9 is a side elevational view of another staple usable in an endoscopic stapling device, showing the staple in an opened configuration.

Upon the embedding of opened staple 91 in internal body tissues 100, inner tubular member 88 is pushed in the distal direction to engage staple legs 91a and 91b and thereby close the staple about opening 102. Simultaneously, as illustrated in FIG. 8D, an additional outer tubular member 96 slidably disposed in biopsy channel 84 around tubular member 82 is shifted distally to engage forceps jaws 94a and 94b and thereby close the forceps 94 to aid in the closure of opening 102 during the stapling operation.

In a subsequent step shown in FIG. 4E, outermost tubular member 96 and inner tubular member 88 are retracted into biopsy channel 84. In addition, tubular member 82 is moved proximally to withdraw forceps 94 from body tissues 100. During the retraction of outer tubular member 82 into the endoscope's biopsy channel, forceps jaws 94a and 94b pivot towards one another through a camming action when the jaws slide past the rim or lip at the distal end of biopsy channel 84 or past the mouth of outermost tubular member 96. Finally, rod member 90 is retracted into inner tubular member 88 (FIG. 4F) and the entire endoscopic stapling device is then withdrawn from the patient's body through the aperture through which it was introduced.

Figure 10:
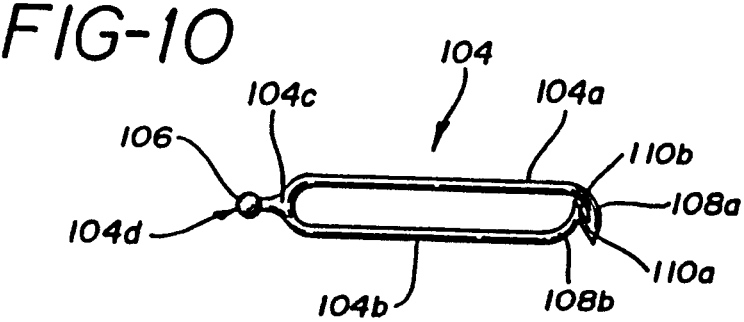
FIG. 10 is a side elevational view of the staple of FIG. 9 in a closed, postfiring configuration.

Another staple 104 usable in an endoscopic stapling device is illustrated in FIGS. 9–12. That staple includes includes a pair of legs 104a and 104b joined by a bight section 104c and provided on a side of the bight section opposite the legs with a projection 104d terminating in a knob or ball 106. Each leg 104a and 104b is provided at a free end with a respective inwardly turned foot 108a and 108b. Foot 108a is formed on an outer, distally facing side with a barb or hook 110a, while foot 108b is provided on an inwardly or proximally facing face with another barb or hook 110b. As illustrated in FIG. 10, hooks 110a and 110b interfit and thereby cooperate with one another to lock the staple in a closed configuration at the end of a stapling operation.

Like legs 54a and 54b of staple 54, legs 104a and 104b of staple 104 are spring biased outwardly. Thus, a force pressing legs 104a and 104b towards one another is required to close staple 104.

Figure 11:
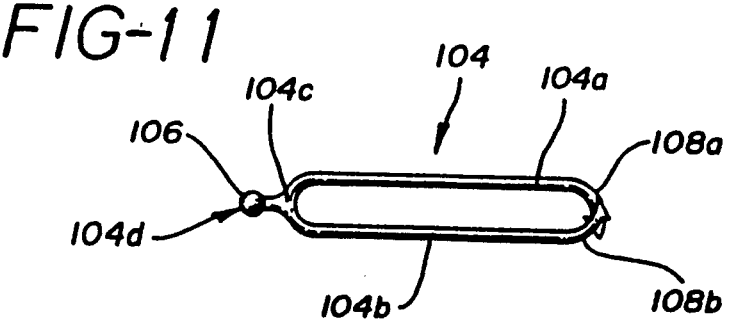
FIG. 11 is a side elevational view of the staple of FIGS. 9 and 10, showing the staple in a closed, prefiring configuration.
Figure 12:
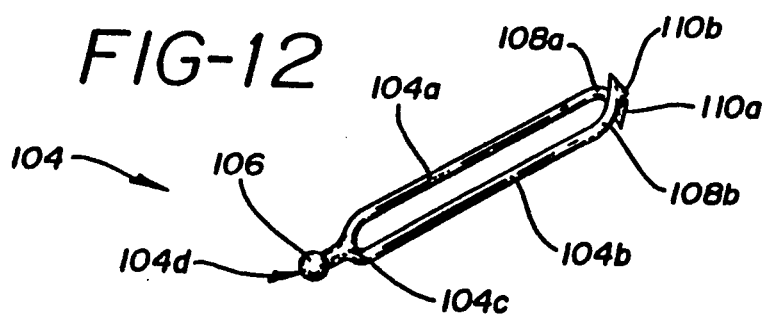
FIG. 12 is a rear perspective view of the staple of FIGS. 9-11, showing the staple in the closed, prefiring configuration.

FIGS. 11 and 12 show staple 104 in the prefiring closed configuration. The staple legs 104a and 104b are disposed side-by-side. When staple 104 is opened upon ejection from a tubular member, legs 104a and 104b spring apart under the action of internal forces (FIG. 9) so that hooks 110a and 110b are aligned with one another.

The staple of FIGS. 9–12 is particularly useful in closing tubular body organs such as blood vessels, sperm ducts, and Fallopian tubes.

Figure 13:
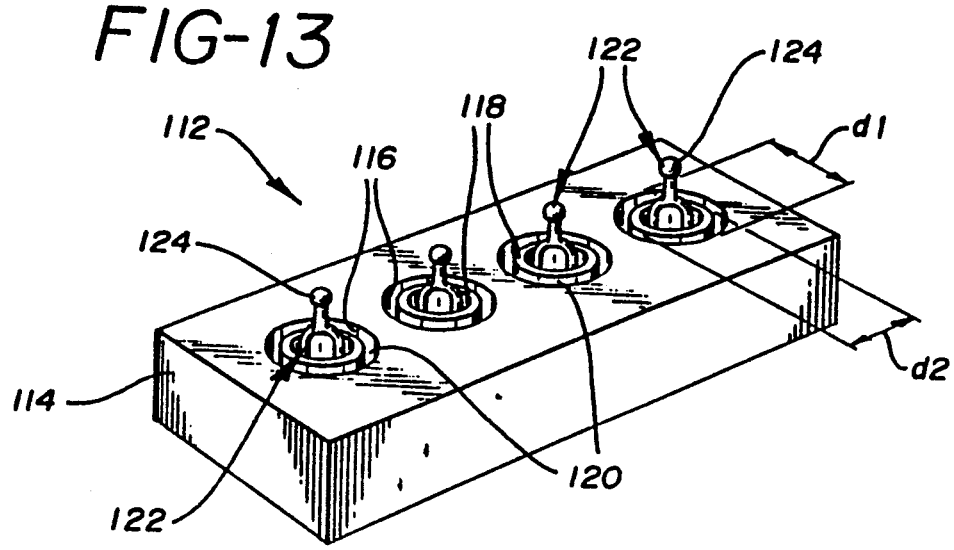
FIG. 13 is an isometric view of a staple package.

As depicted in FIG. 13, a surgical staple package 112 comprises a container 114 provided with a plurality of cylindrical recesses 116 having a common diameter d1. Disposed in each recess 116 is a respective annular sleeve 118. Sleeves 118 have a common outside diameter d2 smaller than diameter d1 of recesses 116, whereby an annular space 120 is formed between each sleeve 118 and the cylindrical wall defining the respective recess 116. A plurality of staples 122 are seated in sleeves 118, each staple 122 being provided with a connector element 124 in the form of a knob, a plate or other cross-sectionally polygonal member for releasably connecting the respective staple to the distal end of a flexible rod member 30, 68, 90 of an endoscopic stapling device. Staples 122, whether in the specific form of staple 32, 54, or 104 or some other form consistent with the principles of the invention, are placed in a prefiring closed configuration in sleeves 118.

Figure 14:
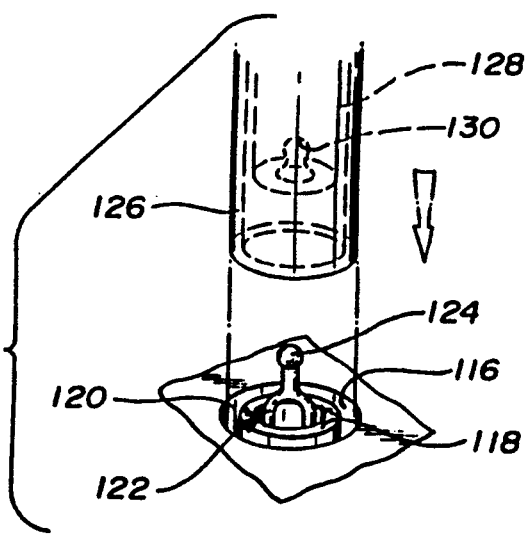
FIGS. 14 and 15 are essentially isometric views of a staple in the package of FIG. 13, showing successive steps in the removal of the staple from the package and the simultaneous loading of the staple into an endoscopic stapling device.
Figure 15:
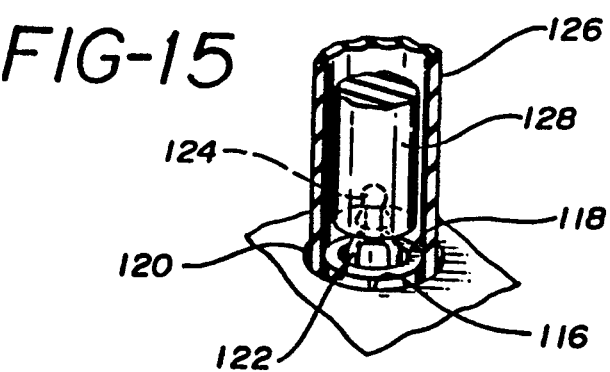
Figure 21A:
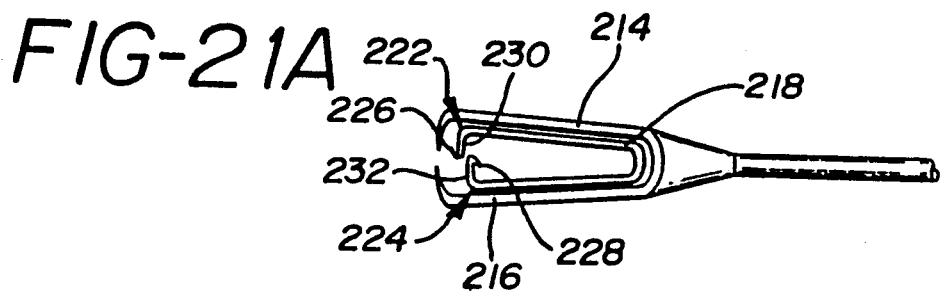
FIGS. 21A through 21D are schematic partial side elevation views showing successive steps in the operation of another endoscopic stapling device like the device of FIGS. 16-19.
Figure 21B:
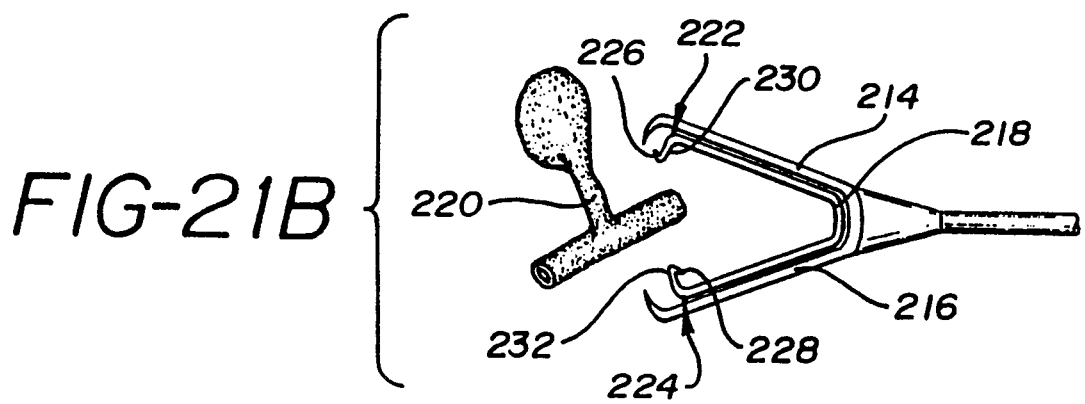
Figure 21C:
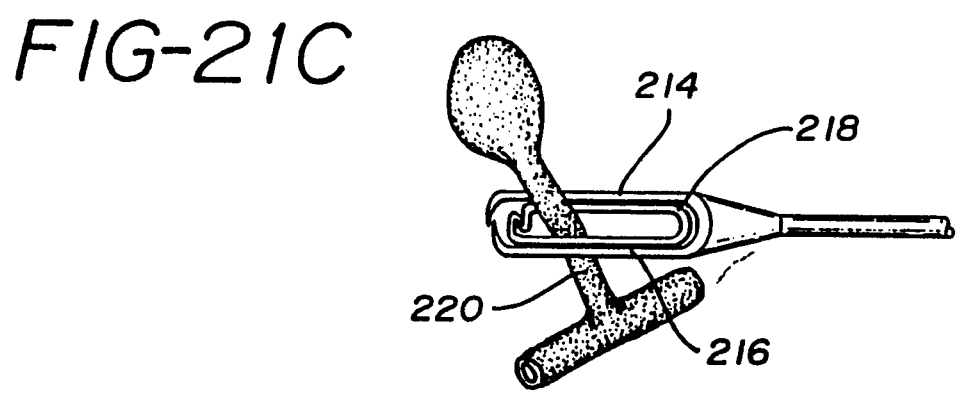
Figure 21D:
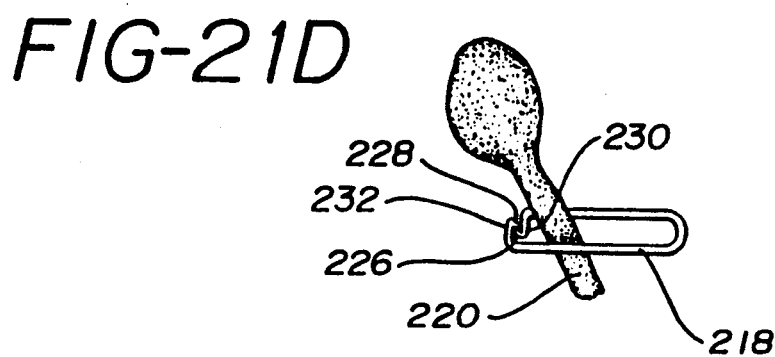

Annular spaces 120 have a width and a diameter sufficiently large so that the annular spaces can each receive the distal end of an inner tubular member 28, 66, 88 of an endoscopic stapling device. As illustrated in FIGS. 14 and 15 to load a staple 122 from package 112, the distal end of a flexible tubular member 126 of an endoscopic stapling device in accordance with the invention is inserted into the annular space 120 about the respective staple. Subsequently, a flexible rod member 128 of the endoscopic stapling device is moved distally through tubular member 126 until a recess 130 at the distal end of rod member 128 receives connector element 124, releasably securing the staple 122 to rod member 128. Tubular member 126 is then withdrawn from the annular space 120 and the staple 122 removed from its respective sleeve 118. The entire endoscopic stapling device is then inserted into the biopsy channel of an endoscope. It is to be understood that, should the need arise for more than one staple to close an internal opening, an endoscopic stapling device in accordance with the invention may be removed from the endoscope's biopsy channel and reloaded with another staple while the endoscope remains partially inserted in the patient's body.

As illustrated in FIG. 16, another endoscopic stapling device comprises an elongate flexible outer tubular member 140 having a diameter sufficiently small so that the tubular member is slidably insertable into a biopsy channel extending longitudinally through a flexible tubular endoscope. Slidably inserted inside tubular member 140 is an elongate flexible rod member 142 provided at a distal end with an actuator plate 144 formed at a distal end with a pair of substantially colinear camming apertures or slots 146 and 148. Slots 146 and 148 are traversed by respective pins 150 and 152 connected to respective fingers or levers 154 and 156 of a pair of forceps jaws 158 and 160. Tubular member 140, rod member 142, actuator plate 144, fingers 154 and 156, and jaws 158 and 160 form parts of an elongate flexible forceps member 161 slidably insertable through the biopsy channel of an endoscope for performing stapling operations on internal body tissues of a patient without the necessity of opening the patient's body by means of an extensive incision.

Fingers or levers 154 and 156 are pivotably connected to one another by an elongate transversely oriented pin 162 (see FIG. 19) slidably traversing at its ends a pair of longitudinally extending slots or recesses 164 (one shown in FIG. 16) in tubular member 140. Slots 164 serve to limit the motion of jaws 158 and 160 with respect to tubular member 140 and to guide the jaws in longitudinal shifts along tubular member 140.

Jaws 158 and 160 are formed on inwardly facing surfaces with respective longitudinal grooves 166 and 168 in which legs 170 and 172 of a staple 174 are seated. Staple 174 has a spring bias construction tending to force the staple into an opened configuration. However, prior to the ejection and application of staple 174 during a surgical operation, the staple is maintained between jaws 158 and 160 in a closed prefiring configuration through its seating in grooves 166 and 168.

Distal ends of jaws 158 and 160 are formed with teeth 173 and 175 for gripping or grasping internal body tissues at a surgical site, to pull the tissues together and to maintain them in a bunched state during a stapling operation.

Legs 170 and 172 of staple 174 are provided on inwardly facing sides with a pair of locking elements 176 and 178 formed on distal and proximal sides with respective hooks 180 and 182 and having smooth surfaces 184 and 186 on the opposing sides. In the closed prefiring configuration of FIGS. 16 and 17, smooth surfaces 184 and 186 engage one another and assist in retaining staple 174 in a deformed state.

During a stapling operation, rod member 142 is pushed in a distal direction through tubular member 140, thereby sliding pin 162 along slots 16 until pin 164 contacts the distal ends of the slots. At that time, jaws 158 and 160 have attained their most distal position with respect to tubular member 140. Continued motion of rod member 142 in the distal direction pivots fingers or levers 154 and 156 about pin 162, which remains fixed at the distal end of slots 164, in opposition to a restoring torque exerted on fingers or levers 154 and 156 by a tension spring 188. The pivoting of fingers or levers 154 and 156 also pivots jaws 158 and 160 from the closed configuration of FIGS. 16 and 17 to the opened configuration of FIG. 18. The opening of jaws 158 and 160 allows staple 174 to open under its own internal biasing forces from the closed prefiring configuration of FIGS. 16 and 17 to an opened firing-ready configuration of FIG. 18. As indicated in FIG. 18, legs 170 and 172 of staple 174 shift relative to one another upon an opening of the staple so that locking elements 176 and 178 can lock upon a closing of staple 174 under the pressure exerted by jaws 158 and 160 during a closing thereof. Jaws 158 and 160 ar closed by pushing tubular member 140 in the distal direction while maintaining the position of jaws 158 and 160 with respect to an internal surgical site.

As illustrated in FIG. 20A, a stapling operation commences with inserting a tubular endoscope member 190 through an aperture (not illustrated) in a patient's body (not illustrated). The endoscope is used to visually locate internal body tissues 192 inside the patient's body which require a surgical operation. Upon locating the surgical site, a surgeon pushes an elongate flexible forceps member 194 in a distal direction through a biopsy channel 196 in tubular endoscope member 190. The shifting of forceps member 194 results in an ejection from biopsy channel 196 of a staple 198 stored in a closed configuration between jaws 200 and 202 of forceps member 194 inside the biopsy channel at a distal end thereof. Forceps member 194 may take the form of forceps 161 or any similar forceps wherein a staple having an open bias is seated between forceps jaws, preferably but not necessarily in grooves provided in the jaws. Staple 198 preferably takes the form of staple 174 and has locking hook elements 204 and 206 for locking the staple in a closed configuration upon disposition thereof in body tissues 192 on opposite sides of a wound 208.

Upon ejection of staple 198 from channel 196, the surgeon opens jaws 200 and 202 of forceps member 194, for example, by pushing an elongate flexible rod member 142 (FIGS. 16-19). The opening of jaws 200 and 202 permits staple 198 to open from a closed prefiring configuration to an opened configuration (FIG. 20B). Forceps member 194 is then pushed further in the distal direction to move the opened staple 298 and jaws 200 and 202 into internal body tissues 192, as shown in FIG. 20C. Upon contact between jaws 200 and 202 and the internal body tissues 192, the surgeon operates forceps member 194 to close the jaws, thereby grasping the internal body tissues between gripping teeth 210 and 212 of jaws 200 and 202 and closing staple 198 in the body tissues about wound 208.

The closing of staple 198 automatically locks the staple in the closed configuration owing to locking hook elements 204 and 206. Upon the locking of staple 198, the surgeon opens jaws 200 and 202 to release said internal body tissues. The forceps member 194 is then retracted into the biopsy channel 196 of endoscope member 190, which is then withdrawn from the patient.

The opening and closing of jaws 200 and 202 may be accomplished as described hereinabove with reference to FIGS. 16-19 or by any other means suitable in the art.

FIGS. 21A through 21D illustrate the use of an endoscopic stapling device with forceps jaws 214 and 216 and an open-biased staple 218 to close a duct 220 in a patient's body. Staple 218 is provided with locking elements 222 and 224 having distally and proximally facing hooks 226 and 228 which engage one another to lock the staple upon closure thereof about duct 220. Locking elements 222 and 224 having proximally and distally facing smooth surfaces 230 and 232 which contact one another in the closed prefiring configuration of staple 218.

As illustrated in FIG. 22, another endoscopic stapling device comprises a pneumatic or hydraulic cylinder 234 operatively connected to forceps jaws 236 via a schematically indicated plunger and linkage mechanism 238 which may be similar to actuator plate 144, slots 146 and 148, pins 150 and 152, and fingers or levers 154 and 156. Cylinder 234 is fed with pressurized air or liquid from a reservoir or source 240 via a manually operable valve 242.

A staple 174, 198 or 218 is loadable between respective forceps jaws by withdrawing the entire flexible forceps from the endoscopic member with which the forceps is being used.

As illustrated schematically in FIGS. 23A, 23B and 23C, an endoscopic or laparoscopic surgical instrument comprises an elongate holder in the form of an elongate tubular member 244 which defines an elongate receptacle or chamber 246. Receptacle 246 is substantially rectangular in transverse cross-section for receiving a plurality of identical surgical staples 248 in accordance with the invention. Each staple 248 has a spring bias tending to force the staple into an opened configuration and is disposed in a closed prefiring configuration in the holder 244. The staples are lined up end to end in holder 244 to form a linear magazine. A mechanism in the form of a compressed helical spring 250 is provided at the proximal end of receptacle or chamber 246 for advancing the staples 248 in a distal direction towards a pair of forceps jaws 252 upon a firing of a most distal staple 254 which is disposed in grooves (not illustrated) in the jaws.

It is to be noted that in the schematic illustration of FIGS. 23A-23C, staples 248 are shown as being spaced from one another for purposes of clarity in the drawing. In actuality, staples 248 contact each other at their proximal and distal ends, whereby spring 250 is able to push the entire magazine in the distal direction to load staples 248 successively into jaws 252. In addition, jaws 252 are schematically illustrated as being swingably attached to holder 244 at pivot points 256.

As depicted particularly in FIG. 23B, forceps jaws 252 are designed to block staples 248 from advancing in holder 244 upon an opening of the forceps jaws. This blocking action is implemented by the shape of jaws 252 and their mounting relative to holder 244. (See description hereinafter with reference to FIG. 24.) Forceps jaws 252 are manually actuated via one or more grips 258 at the proximal end of the instrument. It is to be understood that the tubular holder 244 is dimensioned for insertion into the biopsy channel of an endoscope or laparascope.

Upon an opening of jaws 252, foremost staple or clip 254 opens automatically under the action of its spring bias. As discussed hereinabove with reference to other embodiments of the invention, staple 254 is then closed about a wound, incision or tear 260 in internal body tissues 262, as illustrated in FIG. 23C. During a closure of jaws 252, in which staple 254 is applied to the internal tissues 262, the staples 248 in holder 244 are blocked from distally advancing because of the continued presence of foremost staple 254 inside jaws 252. After staple 254 has been applied to the wound 260 and locked or otherwise permanently closed, jaws 252 are opened and withdrawn from around the applied staple 254. During this removal of forceps jaws 252, the advance of staples 248 in the distal direction is prevented by the opened jaws themselves, as described above. Upon a subsequent closure of forceps jaws 252, staples 248 slide in the distal direction under the pressure exerted by helical spring 250. The endoscopic or laparoscopic surgical device of FIGS. 23A-23C is then ready for another staple application operation.

FIGS. 24A-24C illustrate successive steps in the operation of another endoscopic or laparoscopic surgical device. The device of FIGS. 24A-24C has the same structure and operates in the same manner as the instrument of FIGS. 23A-23C, except that the staple advance mechanism takes the form of a manually actuated push rod 264 instead of helical spring 250. Push rod 264 is moved in the distal direction to advance staples 248 towards jaws 252 upon the application of staple 254 to body tissues.

Figure 25:
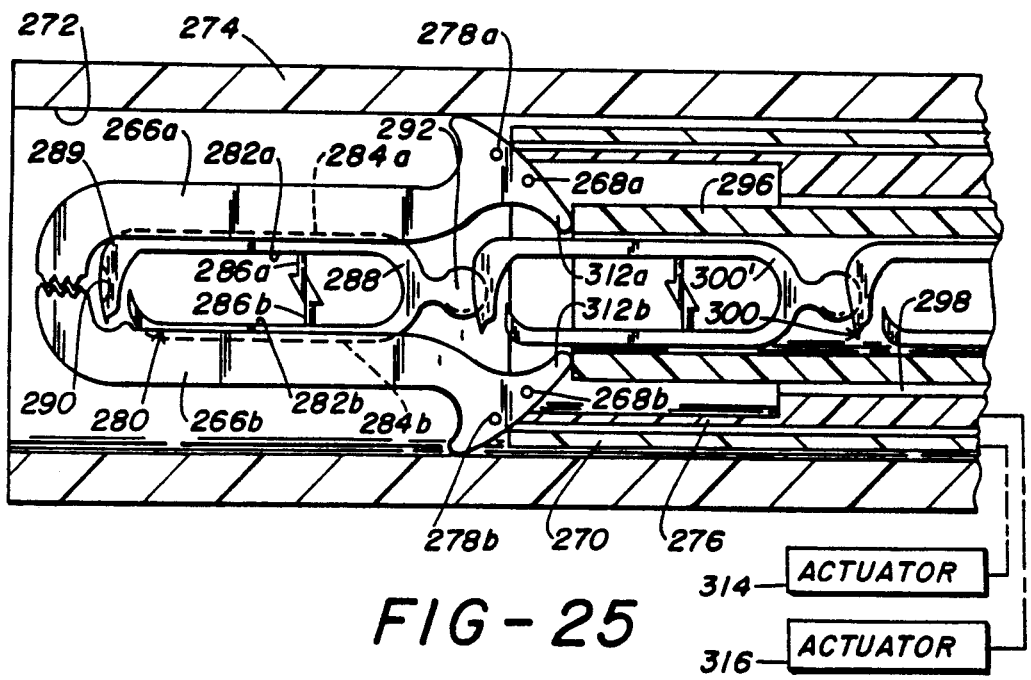
FIG. 25 is a partial longitudinal cross-sectional view, on an enlarged scale, of a distal end of yet another endoscopic or laparoscopic staple applicator with a staple magazine.

As depicted in FIG. 25, a pair of forceps jaws 266a and 266b are pivotably connected via respective pins 268a and 268b to a tubular forceps frame 270 slidably inserted inside a biopsy channel 272 of an endoscopic instrument 274, e.g., a flexible endoscope or a laparoscopic member. Jaws 266a and 266b are manipulated between a closed position illustrated in FIG. 25 and a non-illustrated opened position via a tubular actuator member 276 slidably inserted inside tubular forceps frame 270. At their proximal ends, forceps jaws 266a and 266b are hingedly secured to a distal end of actuator member 276 at respective pivot points 278a and 278b.

As further depicted in FIG. 25, a foremost staple 280 has a pair of legs 282a and 282b seated in grooves 284a and 284b in respective forceps jaws 266a and 266b. As discussed hereinabove with respect to other staples in accordance with the invention, legs 282a and 282b are provided with respective hook-shaped locking elements 286a and 286b. Legs 282a and 282b are connected to one another by a bight portion 288 of staple 280. Bight portion 288 is deformed, in the closed prefiring configuration of staple 280 illustrated in the drawing, so that locking elements 286a and 286b are staggered with respect to their locking position, whereby the staple can be opened upon an opening of jaws 266a and 266b.

Figure 27:
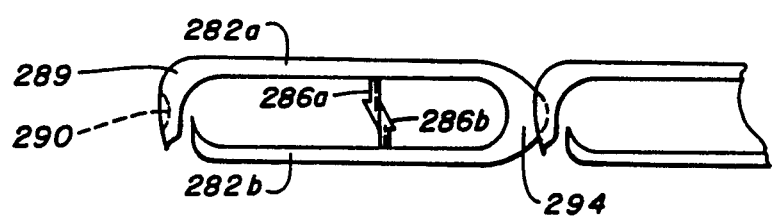
FIG. 27 is a side elevational view of a staple for use with the endoscopic or laparoscopic applicators of FIGS. 23A-23C, 24A-24C, and 25-26.

Leg 282a of staple 280 is formed at a distal end with an inwardly turned finger or tooth 289 provided with a recess 290 for receiving a knob or ball 292 of a more distally located staple. Alternatively, as illustrated in FIG. 27, knob or ball 292 may be replaced by a simply rounded proximal end portion 294. In either case, the recess 290 acts together with knob 292 or rounded end portion 294 to form a universal ball-and-socket-type joint to facilitate a staple advance or loading operation particularly when a flexible endoscopic member is being used in a stapling operation.

Figure 26:
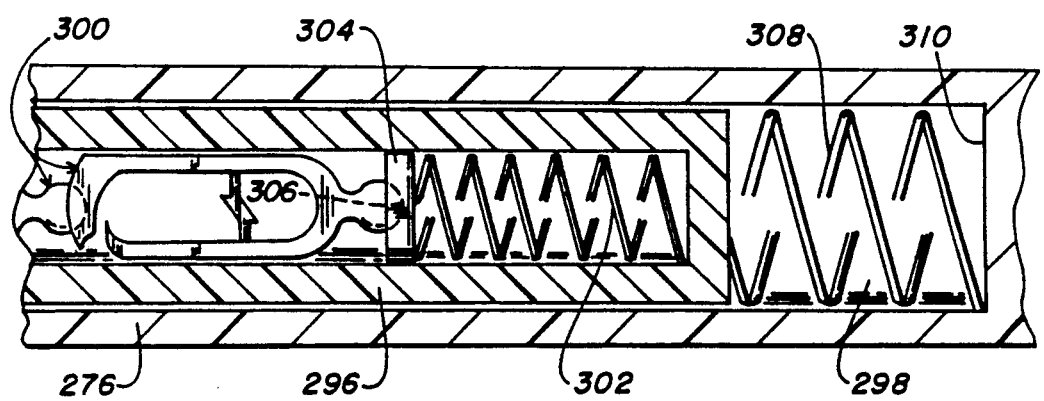
FIG. 26 is a partial longitudinal cross-sectional view, on a larger scale, of an intermediate portion of the endoscopic or laparoscopic staple applicator of FIG. 25.

As further illustrated in FIGS. 25 and 26, a staple cartridge or holder 296 is slidably disposed inside a chamber 298 formed at the distal end of actuator member 276. Cartridge 296 holds a plurality of staples 300 identical to staple 280 in a linear array or magazine wherein the staples 300 are disposed end to end in a common closed prefiring configuration as discussed hereinabove with reference to staple 280 and other staples in accordance with the invention.

As shown in FIG. 26, staples 300 are pushed in a distal direction towards forceps jaws 266a and 266b by a helical compression spring 302 acting via a piston member 304. Piston member is formed on a distal side with a recess 306 for receiving knob 292 of a most proximal staple in the magazine of staples 300. Cartridge 29 in turn is pushed in the distal direction by another helical spring 308 which is compressed between a proximal end of cartridge 296 and a transverse surface 310 in part defining chamber 298. As shown in FIG. 25, spring 308 holds cartidge 296 against wings or extensions 312a and 312b at the proximal ends of forceps jaws 266a and 266b.

Upon insertion of endoscopic instrument 274 inside a patient's body, either through a natural opening such as the mouth or rectum or through an aperture formed in the patient's abdominal wall or elsewhere during a laparoscopic procedure, and upon visual detection of an internal wound, incision or other tissue abnormality requiring closure, tubular frame 270 and actuator member 276 are moved distally via operation of respective actuators 314 and 316. Actuators 314 and 316 may be hydraulic circuits or manual actuators or may take any other form known in the art for operating a forceps at the distal end of an endoscopic surgical instrument. Tubular frame 270 and actuator member are preferably moved on tandem so that forceps jaws 266a and 266b remain temporarily in the closed configuration.

Upon juxtaposition of jaws 266a and 266b to the surgical site, actuators 314 and 316 are operated so that forceps frame 270 remains fixed while actuator member 276 is shifted in the proximal direction, whereby jaws 266a and 266b are pivoted about pins 268a and 268b and staple 280 is concomitantly opened. During the pivoting of jaws 266a and 266b about pins 268a and 268b, opening the jaws, wings or extensions 312a and 312b rotate inwardly towards one another, thereby pinching the first or most distal staple 300' in the magazine of staples 300 and preventing the entire staple magazine from moving. Wings or extensions 312a and 312b could be alternatively configured to engage the first magazine staple 300' at a distal end of the staple, thereby blocking the distal advance of that staple and the other staples 300 in the magazine in cartridge 296.

Upon the opening of jaws 266a and 266b and staple 280, actuators 314 and 316 are then operated to shift the opened jaws and the staple further in the distal direction to engage the internal body tissues which are to be closed. When the tissues are properly engaged, actuators 314 and 316 are operated to move actuator member 276 distally relative to forceps frame 270, thereby closing jaws 266a and 266b and staple 280 in opposition to the internal spring bias of the staple. As described above, closing the staple brings locking elements into a locking engagement with one another to maintain staple 280 in a closed configuration.

Upon the locking of staple 280, jaws 266a and 266b are again opened through a suitable operation of actuators 314 and 316. The opening of jaws 266a and 266b pinches staple 300' and prevents it from moving forward under the force of spring 302 until the jaws have been closed again. Upon the closing of jaws 266a and 266b and the consequent shifting of staples 300 to load the jaws with staple 300', the endoscopic instrument 274 is ready for the application of another staple to the internal body tissues of the patient.

FIGS. 28A, 28B, 29A, 29B, 30A, 30B, 31A, 31B, 32A-32C, 33A-33C, 34A-34C and 35 all illustrate further embodiments of a surgical staple wherein (a) the legs of the staple are provided with locking elements which cooperate with one another to maintain the staple in a closed postfiring configuration, (b) at least one of the legs and the bight portion of the staple is provided with a spring bias tending to force the legs apart to open the staple, and (c) the staple is disposed in a closed prefiring configuration wherein at least one of the legs, the bight portion, and the two locking elements is deformed to prevent cooperation of the locking elements, whereby the staple may be opened from the closed prefiring configuration.

As shown in FIGS. 28A and 28B, a staple or clip 318 has a pair of legs 320a and 320b joined by a bight or bridging portion 322. Leg 320a is provided on an inside surface, i.e., a surface facing leg 320b, with a first locking element 324 in the form of a cylinder 326 attached to the end of a web 328. Leg 320b is provided on an inwardly facing surface with a female locking element 330 including a cylindrical bore 332 communicating with a slot 334 for insertion of cylinder 326, as shown in FIG. 28B. As illustrated in FIG. 28A, web 328 of locking element 324 is bent in the distal direction in a closed prefiring configuration of staple or clip 318. Web 328 is resilient and assumes a substantially orthogonal configuration upon an opening of staple 318, thereby facilitating the insertion of cylinder 326 through slot 334 into bore 332. Locking element 330 may be formed laterally of slot 334 with beveled or inclined surfaces 336 for guiding cylinder 326 towards slot 334 during a staple closing operation.

The staple or clip 338 of FIGS. 29A and 29B is provided on inwardly facing surfaces of legs 340a and 340b with a first locking element 342 in the form of a cylinder 344 at the end of a resilient arm 346 and a second locking element 348 in the form of an angle provided with a slot 350 for receiving arm 346 in a closed postfiring configuration of the staple shown in FIG. 29B. As illustrated in FIG. 29A, arm 346 of locking element 342 is bent in the distal direction in a closed prefiring configuration of staple or clip 338.

The staple or clip 352 of FIGS. 30A and 30B is provided on inwardly facing surfaces of legs 354a and 354b with a first locking element 356 in the form of a moderately resilient arrowhead 358 at the end of a resilient arm 360 and a second locking element 362 in the form of a pair of angles 364 and 366 which define a slot 368 for receiving arm 360 in a closed postfiring configuration of the staple shown in FIG. 30B. As illustrated in FIG. 30A, arm 360 of locking element 356 is bent in the distal direction in a closed prefiring configuration of staple or clip 352. During a closing stroke of staple 352, arrowhead 358 deforms to enable it to pass through slot 368 and latch onto angles 364 and 366.

Figure 31A:
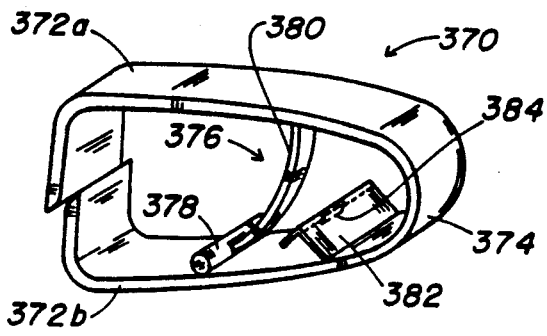
FIGS. 31A and 31B are side perspective views of yet another staple or clip, showing the staple in a closed prefiring and a closed postfiring configuration, respectively.
Figure 31B:
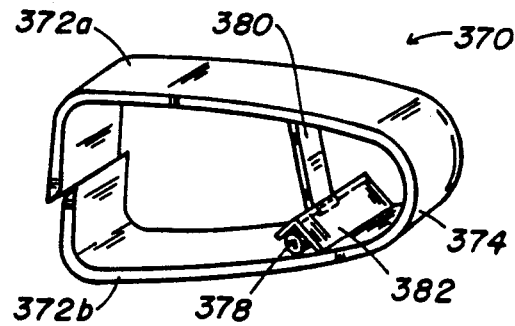

As shown in FIGS. 31A and 31B, another staple or clip 370 has a pair of legs 372a and 372b joined by a bight or bridging portion 374. Leg 372a is provided on an inside surface with a first locking element 376 in the form of a cylinder 378 attached to the end of an arm 380. Leg 372b is provided on an inwardly facing surface with a locking element 382 including an angle formed on a distal side with a slot 384 for receiving arm 380 during an insertion of cylinder 378, as shown in FIG. 31B. As illustrated in FIG. 31A, arm 380 of locking element 376 is bent in the distal direction in a closed prefiring configuration of staple or clip 370. Arm 380 is resilient and assumes a substantially orthogonal configuration upon an opening of staple 370, thereby facilitating the insertion of a free end of arm 380 through slot 384.

Figure 32A:
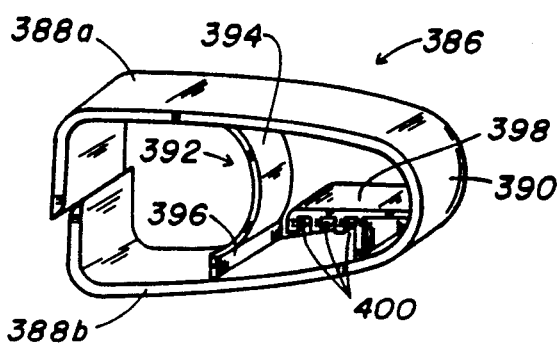
FIGS. 32A, 32B and 32C are side elevational views of a staple, showing the staple in a closed prefiring, an opened and a closed postfiring configuration, respectively.
Figure 32B:
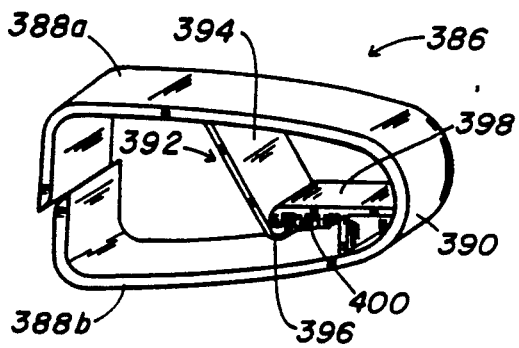
Figure 32C:
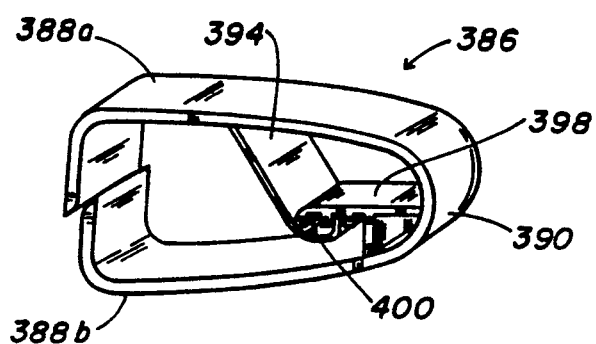

FIGS. 32A, 32B and 32C illustrate a closed prefiring configuration, a first closed postfiring configuration and a second closed postfiring configuration, respectively, of another staple or clip 386. Staple 396 has two legs 388a and 388b joined to one another by a bight or connecting portion 390. Connected to leg 388a is a first locking element 392 including resilient arm 394 formed at a free end with a hook or flange 396. In the closed prefiring configuration of FIG. 32A, arm 394 is bent so that hook 396 is spaced from a second locking element 398. Locking element 398 is provided with a plurality of notches 400 for alternatively receiving hook 396 to lock the staple 386 with different amounts of tension or closure. FIG. 32C shows a staple closed configuration exhibiting a greater tension or degree of closure than the closed configuration of FIG. 32B.

Figure 33A:
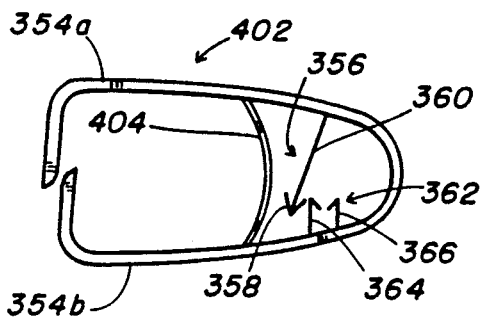
FIGS. 33A, 33B and 33C are side perspective views of another staple or clip, showing the staple in a closed prefiring, an opened and a closed postfiring configuration, respectively.
Figure 33B:
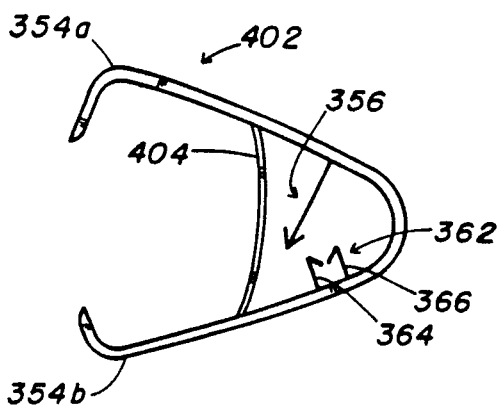
Figure 33C:
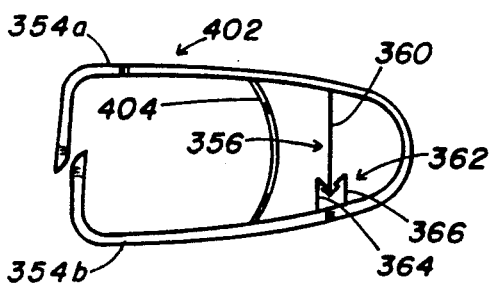

A staple 402 illustrated in closed prefiring, opened and closed postfiring configurations in FIGS. 33A, 33B and 33C, respectively is essentially identical to staple 352 of FIGS. 30A and 30B except that staple 402 is additionally provided with a flexible web 404 extending from one leg 354a to the other leg 354b distally of locking elements 356 and 362. Web 404 serves to shield locking elements 356 and 362 from an invasion or interference of internal tissues during a stapling operation (see FIG. 35). Except for web 404, all the structures of staple 402 are labeled with the same reference numerals as the corresponding parts of staple 362.

Figure 34A:
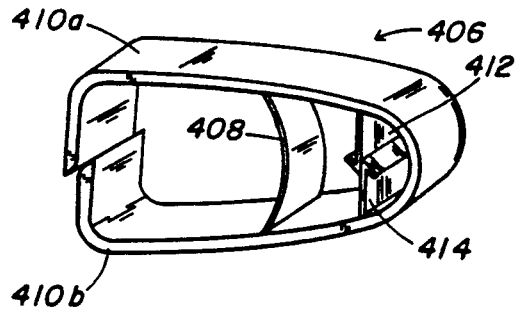
Figure 34B:
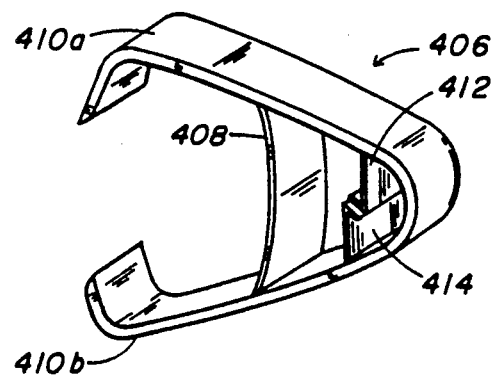
Figure 34C:
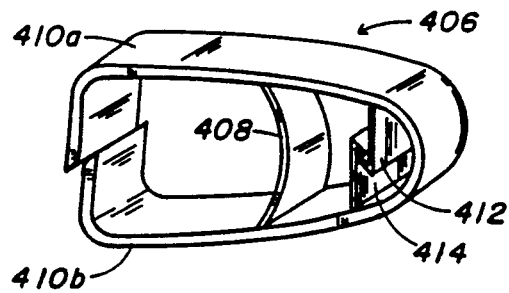
Figure 35:
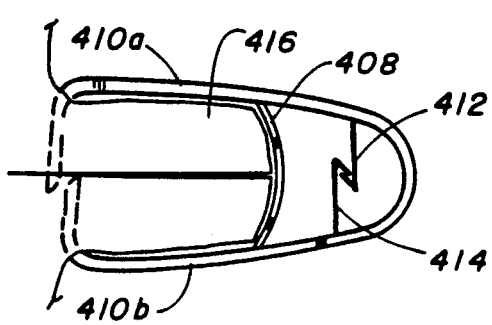
FIG. 35 is a side elevational view of the staple or clip of FIGS. 33A-33C, showing the staple in a closed postfiring configuration about a piece of body tissue.

FIGS. 34A, 34B and 34C illustrate closed prefiring, opened and closed postfiring configurations of a staple 406 substantially the same as staple 280 or 300' and staples 300 of FIGS. 25 and 26. Like staple 402 of FIGS. 33A-33C, staple 406 is supplementarily provided with a flexible web 408 extending from one leg 410a to the other leg 410b distally of hook shaped locking elements 412 and 414. Web 408 serves to shield locking elements 412 and 414 from an invasion or interference of internal tissues 416 during a stapling operation, as illustrated in FIG. 35.

It is to be understood that any of the staples disclosed herein which have locking elements at a proximal or bight end of the staple may be provided with a protective web like web 404 and 408 for preventing the internal body tissues of the patient from interfering with the cooperation of locking elements on the staples during a staple closure operation.

It is to be noted than any of the staples or clips of FIGS. 28A, 28B, 29A, 29B, 30A, 30B, 31A, 31B, 32A-32C, 33A-33C, 34A-34C and 35 may be used in an endoscopic or laparoscopic stapling device. Staples or clips 318, 338, 352, 370, 386 may be formed, like staples 280 and 300 of FIGS. 25-27, with a recess or a protuberance at a distal end and a protuberance or a recess at a proximal end to facilitate a staple advance or loading operation particularly when a flexible endoscopic member is being used in a stapling operation. Other shapes for the distal and proximal ends of the staples are possible which would also facilitate the staple advance or loading operation.

Figure 36A:
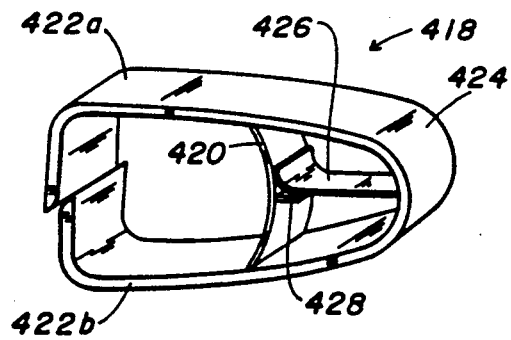
FIGS. 36A and 36B are side perspective views of another staple or clip, showing the staple in a closed prefiring and an opened configuration, respectively.
Figure 36B:
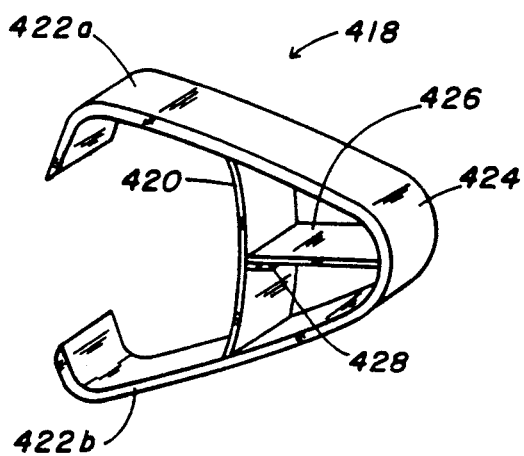
Figure 36C:
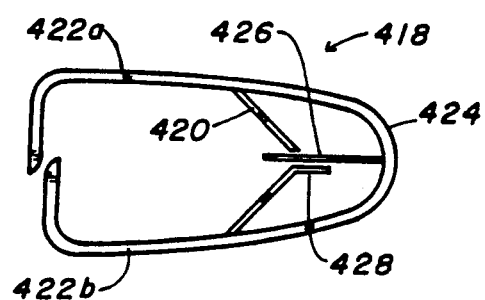
FIG. 36C is a side elevational view of the staple or clip of FIGS. 36A and 36B, in a closed postfiring configuration.

Another staple 418 utilizable in an endoscopic or laparoscopic stapling device is illustrated in FIGS. 36A-36C. In contrast to the above-described staples which have a spring bias tending to open the staple and locking elements for effectuating a closure of the respective staples in opposition to the spring bias, staple 418 has an internal spring bias which tends to close the staple. Staple 418 is provided with an auxiliary spring element 420 extending between legs 422a and 422b. Spring element 420 has a spring bias which tends to open the staple in opposition to the internal spring bias of the staple itself, the spring force exerted by element 420 being greater than the spring force exerted by the internal spring bias of staple 418. Staple 418 is further provided on a bight portion 424 with a distally extending fracture member 426 of limited flexibility. In a closed prefiring configuration of staple 418, shown in FIG. 36A, fracture member 426 is held in a deformed state by a projection 428 extending from a proximal side of spring element 420. Upon an opening of staple 418 by an opening of forceps jaws, as described hereinabove, projection 428 is retracted from fracture member 426 owing to an extension and straightening of spring element 420. Fracture member 426 consequently assumes a straightened configuration, shown in FIGS. 36B and 36C. Upon a subsequent closure of staple 418, through a closing of forceps jaws in which the staple is seated, fracture member 426 breaks or ruptures spring element 420, as shown in FIG. 36C, thereby allowing the internal spring bias of staple 418 to close the staple about internal body tissues of a patient. In this embodiment, spring element 420 is advantageously provided with a score line (not shown) in the region of projection 428 and fracture member 426, to facilitate the rupture of the spring element.

Figure 37:
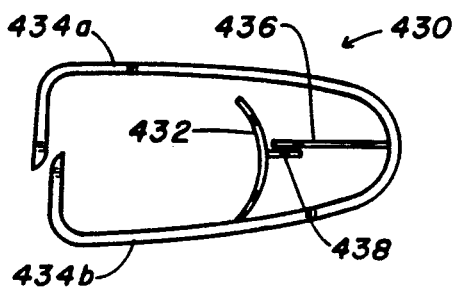
FIG. 37 is a side elevational view of yet another staple or clip, in a closed postfiring configuration.

In another embodiment, illustrated in FIG. 37, a staple 430 is provided with an auxiliary spring element 432 which is attached to one leg 434a of the staple, but is disconnected from the other leg element 434b. Upon an opening of staple 430, a pressure element 436 of limited flexibility straightens from a bent prefiring configuration in which the pressure element is maintained by a projection 438 on a proximal side of spring element 432. During a subsequent staple closing procedure, the straightened pressure element 436 pushes spring element 432 out of contact with leg 434b, whereby an internal spring bias of staple 430 closes and locks the staple.

Staples 418 and 430 are similar to other staples described hereinabove in that staples 418 and 430 are opened by a spring bias. Staples 418 and 430 differ from those other staples in that staples 418 and 430 are held closed by a spring bias rather than by cooperating locking elements.

Figure 38:
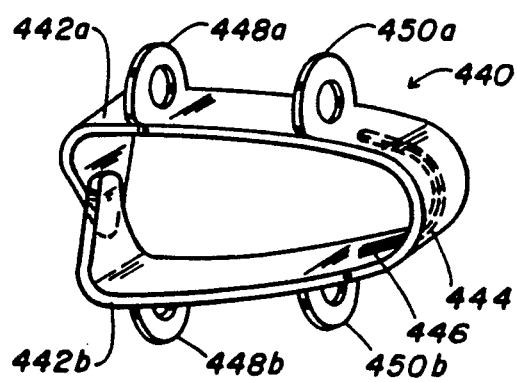
FIG. 38 is a side and front perspective view of another surgical staple for use in endoscopic applications.

As depicted in FIG. 38, another surgical staple 440 comprises a pair of legs 442a and 442b connected to one another by a bight portion 444. A spring element 446 is connected to the staple 440 at bight portion 444 for providing a spring bias tending to close staple 440. Legs 442a and 442b are provided on their outer sides with outwardly extending rings or loops 448a, 450a and 448b, 450b which are used to pull the staple legs apart, as described below.

Figure 39:
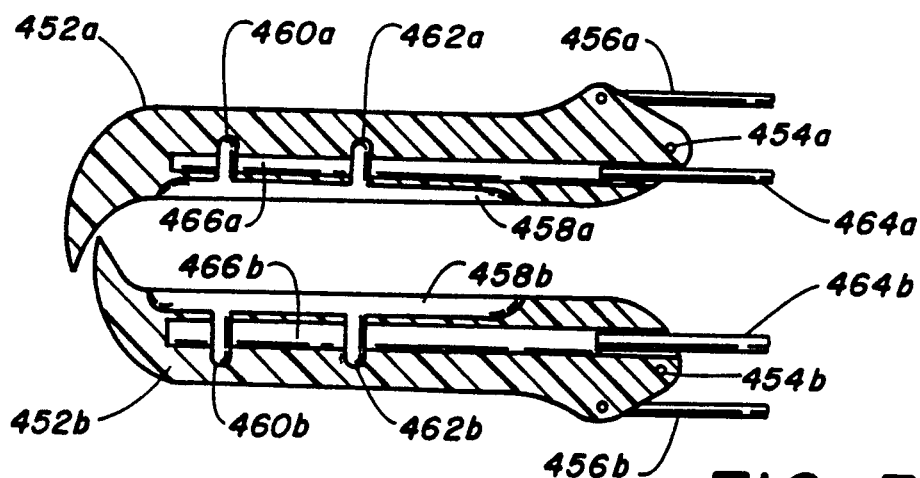
FIG. 39 is a longitudinal cross-sectional view of forceps jaws for applying the staple of FIG. 38 in an endoscopic or laparoscopic surgical operation.
Figure 40:
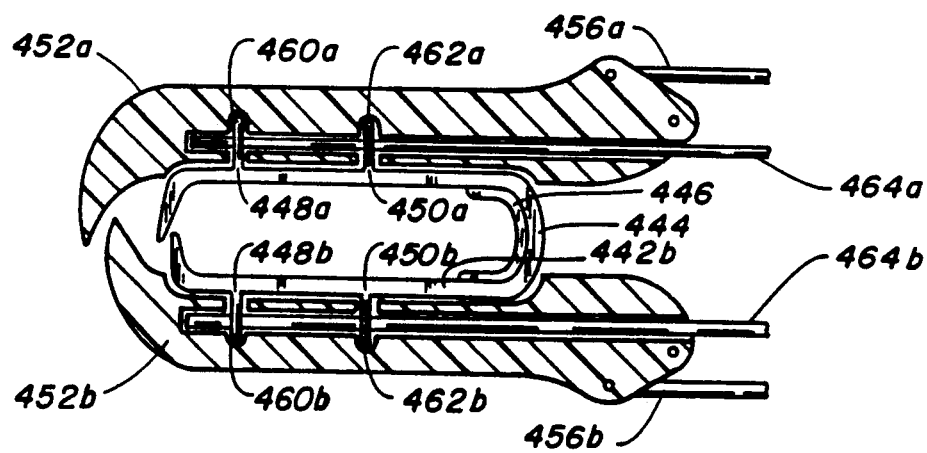
FIG. 40 is a longitudinal cross-sectional view of the staple of FIG. 38 seated in the forceps jaws of FIG. 39, with locking rods in place for entraining the staple to the forceps jaws.

As illustrated in FIGS. 39 and 40, a forceps for applying staple 440 to internal body tissues in an endoscopic or laparoscopic surgical procedure comprises a pair of jaws 452a and 452b pivotably linked to an elongate tubular frame member (not shown) via respective linking pins 454a and 454b. Alternate opening and closing of jaws 452a and 452b are controlled by actuator elements 456a and 456b. Jaws 452a and 452b are provided on their inwardly facing sides with respective grooves 458a and 458b for receiving legs 442a and 442b of staple 440. In additional each jaw 452a and 452b is provided with a pair of transversely oriented recesses 460a, 462a and 460b, 462b for receiving rings 448a, 450a and 448b, 450b, respectively.

Upon a disposition of staple 440 in forceps jaws 452a and 452b so that legs 442a and 442b are seated in grooves 458a and 458b and so that rings 448a, 450a and 448b, 450b are inserted into recesses 460a, 462a and 460b, 462b, a pair of locking rods 464a and 464b are shifted in the distal direction through longitudinally extending bores 466a and 466b in jaws 452a and 452b. Rods 464a and 464b also pass through rings 448a, 450a and 448b, 450b, as illustrated in FIG. 40, thereby fastening staple legs 442a and 442b to jaws 452a and 452b.

Upon the completion of the insertion stroke of locking rods 464a and 464b, the staple may be forced into an opened configuration by a relative proximal motion of actuator elements 456a and 456b which pivots jaws 452a and 452b. Upon a subsequent application of staple 440 to internal body tissues, locking rods 464a and 464b are retracted and jaws 452a and 452b are opened, enabling a separation of the forceps jaws from the staple.

Figure 41:
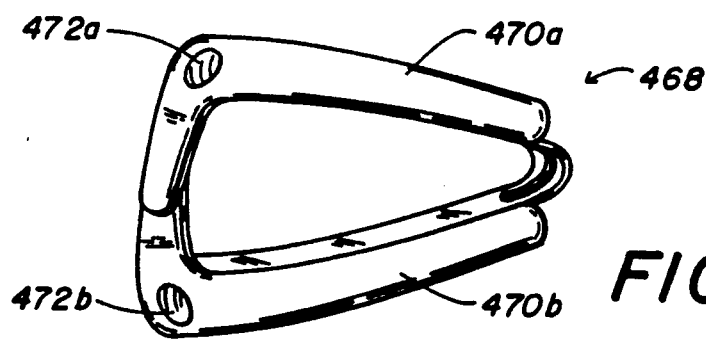
FIG. 41 is a side and front cross-sectional view of another surgical staple.
Figure 42:
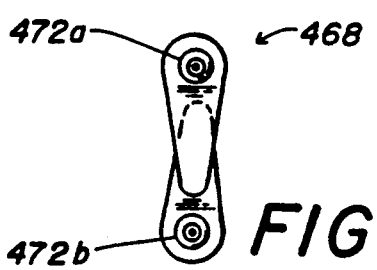
FIG. 42 is a front elevational view of the staple of FIG. 41.
Figure 43:
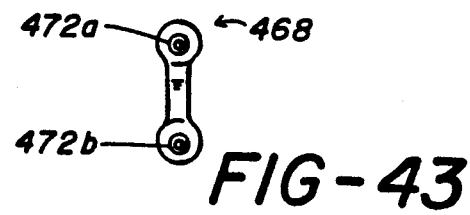
FIG. 43 is a rear elevational view of the staple of FIGS. 41 and 42.

As shown in FIGS. 41-43, another staple 468 which functions according to the same principle as staple 440 of FIG. 38 includes a pair of legs 470a and 470b provided with respective longitudinally extending holes 472a and 472b which are traversed by respective locking rods (not shown) similar to rods 464a and 464b of FIGS. 39 and 40. Staple 468 is also provided with an internal spring bias or an auxiliary spring element 474 tending to force the staple into the closed configuration shown in the drawing.

Figure 44B:
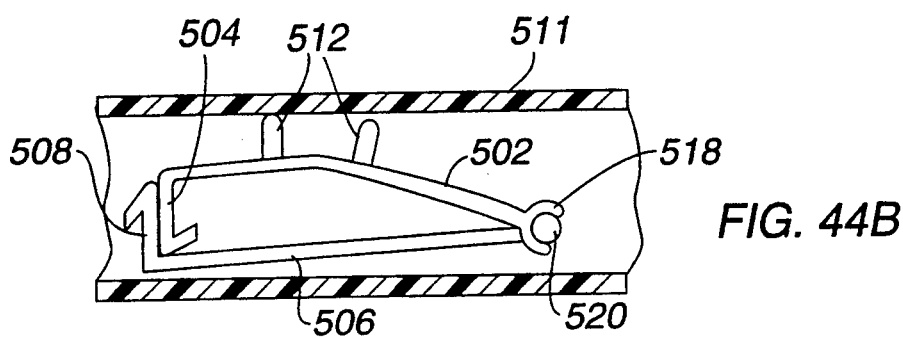
FIG. 44B is a schematic side elevational view of the staple of FIG. 44A in a closed prefiring configuration inside a tubular staple assembly member.

As illustrated in FIG. 44A, a surgical staple 500, particularly but not exclusively for use in endoscopic or laparoscopic surgery as described hereinabove, comprises a first leg 502 provided at a forward or distal end with a hook-shaped locking element 504, a second leg 506 also provided at a forward or distal end with a hook-shaped locking element 508, and a hinge 510 joining the first leg and the second leg to one another. Locking elements 504 and 508 are designed to cooperate with one another to maintain staple 500 in a closed postfiring configuration, as described above with reference to other staple embodiments. Prior to an endoscopic or laparoscopic stapling operation, staple 500 is disposed in a closed prefiring configuration inside a biopsy channel of an endoscope or in a laparoscopic tubular member 511, wherein at least one staple leg 502 or 506 or one of the staple locking elements 504 or 508 is deformed to prevent cooperation of the locking elements, as illustrated in FIG. 44B.

Staple legs 502 and 506 are provided with latching elements in the form of loop-shaped eyelets 512 and 514. Eyelets 512 and 514 cooperate with locking elements, e.g., rods 464a and 464b of FIGS. 39 and 40, to enable a pivoting of legs 502 and 506 away from one another and about hinge 510 during a staple opening operation, as indicated by an arrow 515. Alternatively, the latching elements on staple legs 502 and 506 may take the form of snap-lock projections such as knobs or cooperating snap-lock-type recesses (see FIG. 45).

Hinge 510 is a rotary type hinge essentially free of internal stresses. More specifically, hinge 510 includes a pair of slotted sleeve-type elements 516 and 518 on staple leg 502 and a shaft or pin type element 520 on leg 506. Pin 520 is inserted through slotted sleeves 516 and 518.

A plurality of staples 500 are loaded into a tubular endoscopic or laparoscopic magazine such as holder 244 in FIGS. 24B and 24C. The tubular holder surrounds the staples and maintains the staples in the closed prefiring configuration.

Figure 45B:
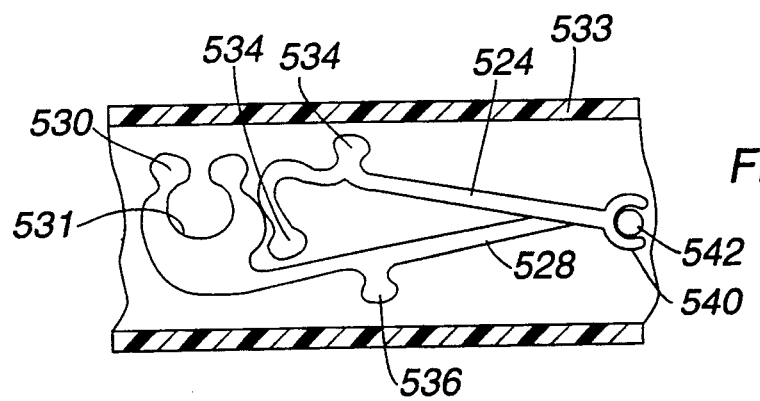
FIG. 45B is a schematic side elevational view of the staple of FIG. 45A in a closed prefiring configuration inside a tubular staple assembly member.

As illustrated in FIG. 45A, another surgical staple 522 comprises a first leg 524 provided at a forward or distal end with a male locking element 526 in the form of a bead or knob projection, a second leg 528 provided at a forward or distal end with a female locking element 530 with a groove or recess 531, and a hinge 532 joining the first leg and the second leg to one another. Locking elements 526 and 530 are designed to cooperate with one another to maintain staple 522 in a closed postfiring configuration. Prior to an endoscopic or laparoscopic stapling operation, staple 522 is disposed in a closed prefiring configuration inside a biopsy channel of an endoscope or in a laparoscopic tubular member 533, wherein at least one staple leg 524 or 528 or one of the staple locking elements 526 or 530 is deformed to prevent cooperation of the locking elements, as illustrated in FIG. 45B.

Staple legs 524 and 528 are provided with latching elements in the form of beaded or knob-like projections 534 and 536. Projections 534 and 536 are releasably received into recesses in staple-applying forceps jaws (see FIG. 48) to enable a pivoting of legs 524 and 528 away from one another and about hinge 532 during a staple opening operation.

Hinge 532 is a rotary type hinge essentially free of internal stresses. More specifically, hinge 532 includes a pair of slotted sleeve-type elements 538 and 540 on staple leg 524 and a shaft or pin type element 542 on leg 528. Pin 542 is inserted through slotted sleeves 538 and 540.

A plurality of staples 522 are loaded into a tubular endoscopic or laparoscopic magazine such as holder 244 in FIGS. 24B and 24C. The tubular holder surrounds the staples and maintains the staples in the closed prefiring configuration.

FIG. 46 depicts hinge 510 in greater detail and shows not only slotted sleeve-type elements 516 and 518 on staple leg 502 and a shaft or pin type element 520 on leg 506, but also a neck portion 544 connecting the body of staple leg 506 to pin 520.

Staple hinge 510 or 532 may take the form 546 shown in FIG. 47. Hinge 546 is a rotary type hinge essentially free of internal stresses. Hinge 546 includes a pair of sleeves or collars 548 and 550 on one staple leg 552 and another sleeve or collar 554 on another staple leg 556. Sleeve 554 is inserted between sleeves 548 and 550, and a pin 558 is inserted through the three sleeves. Pin 558 includes a head flange 560 at one end and a rivet or nut 562 connected to pin 558 at the opposite end.

Figure 48:
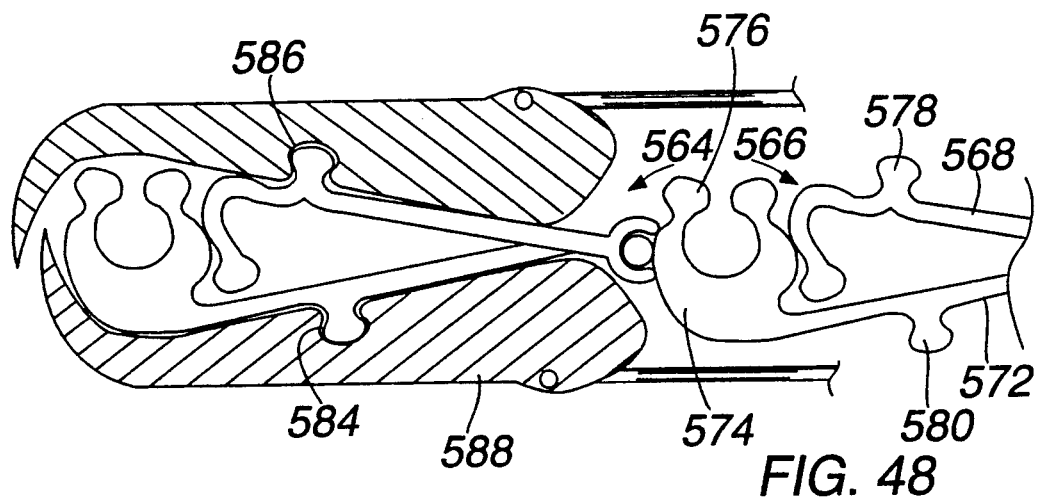
FIG. 48 is a partial longitudinal cross-sectional view, on a greatly enlarged scale, of a staple-applying forceps in accordance with the present invention, showing a pair of entrained staples which are partially deformed in a closed prefiring configuration.

FIG. 48 shows a pair of endoscopic or laparoscopic surgical staples 564 and 566 each in a closed prefiring configuration and aligned end to end with one another at the distal end of an endoscopic or laparoscopic stapling device (not shown), as described above in detail with regard to other embodiments. Each staple is similar to staple 522 (FIG. 45) and includes a first leg 568 provided at a forward or distal end with a male locking element 570 in the form of a bead or knob projection, a second leg 572 provided at a forward or distal end with a female locking element 574 with a groove or recess 531, and a hinge 576 joining the first leg and the second leg to one another. Locking elements 570 and 574 are designed to cooperate with one another to maintain staple 522 in a closed postfiring configuration.

Staple legs 568 and 572 are provided with latching elements in the form of beaded or knob-like projections 578 and 580. Projections 578 and 580 are releasably received into recesses 582 and 584 in staple-applying forceps jaws 586 and 588 to enable a pivoting of legs 568 and 572 away from one another and about hinge 576 during a staple opening operation.

As shown in FIG. 48, prior to an endoscopic or laparoscopic stapling operation, distal-most staple 564 is disposed in a closed prefiring configuration between jaws 586 and 588. Proximal staple 566 is disposed inside a biopsy channel (not illustrated) of an endoscope or in a laparoscopic tubular member (not illustrated). The distal end portion of staple leg 568 is deformed to prevent cooperation of locking elements 570 and 574. Upon an opening of forceps jaws 586 and 588, staple leg 568 resumes a straightened configuration so that locking elements 570 and 574 lockingly mate with one another upon a subsequent closing of forceps jaws 586 and 588. As discussed above, jaws 586 and 588 are provided with seating grooves for receiving legs 568 and 572. In addition, jaws 586 and 588 are designed to enable automatic reloading of the jaws from the proximal direction.

Figures 49, 50:
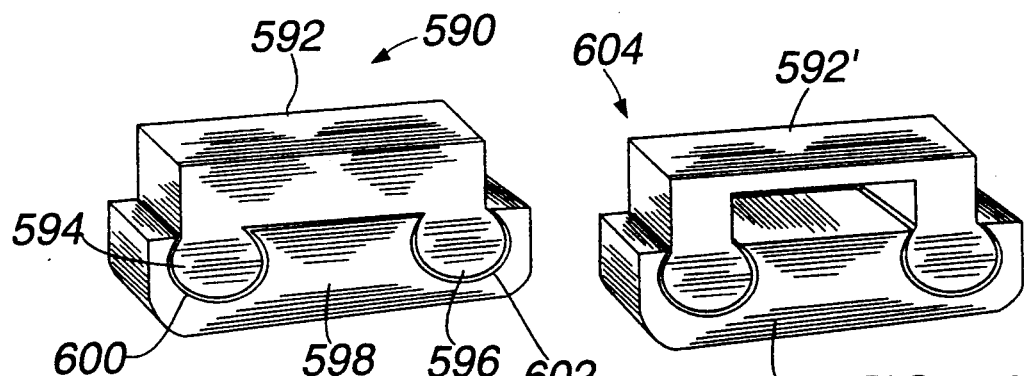
FIG. 49 is a schematic side perspective view, on an enlarged scale, of yet another surgical staple in accordance with the present invention, for use in endoscopic and/or laparoscopic procedures.
FIG. 50 is a view of a modified staple similar to the staple of FIG. 49.

As illustrated in FIG. 49, yet another surgical staple 590 for an endoscopic or laparoscopic stapling device comprises a first leg portion 592 provided with a pair of spaced first locking elements 594 and 596 in the form of beads or ribs and a second leg portion 598 provided with a pair of spaced second locking elements 600 and 602 in the form of grooves or recesses. Beads 594 and 596 cooperate with recesses 600 and 602 to maintain the staple in a closed postfiring configuration, clamped about a piece of a patient's internal body tissues. Because beads 594 and 596 are disposed at opposite ends of staple leg 592, while recesses 600 and 602 are located at opposite ends of staple leg 598, the tissues are clamped between the locking elements.

Staple leg portions 592 and 598 are maintained spaced from one another in a prefiring configuration by a partition, e.g., a membrane (not shown), extending longitudinally through a tubular magazine or staple holder, e.g., holder 244 in FIGS. 24B and 24C. The membrane serves to divide a biopsy channel of an endoscope or laparoscope into two parallel channels, one for guiding a plurality of first staple legs 592 and the other for guiding a plurality of second staple legs 598.

FIG. 50 depicts a surgical staple 604 similar to staple 590 and intended for clamping greater amounts of tissue than staple 590. Accordingly, staple 604 has a thinner body section on one or both of legs 592' and 598', thereby providing a greater space between the legs in the closed postfiring configuration represented in the drawing.

Staples 590 and 604 are provided on their respective leg portions 592, 598 and 592' and 598' with latching elements (not shown in FIGS. 49 and 50) releasably attachable to forceps jaws for controlling staple opening and closure steps during a stapling operation. Such latching elements may take virtually any form including, but not limited to, snap-lock projections (see FIGS. 45, 48, 51) or recesses or loops or eyelets (see FIG. 44).

Figure 51:
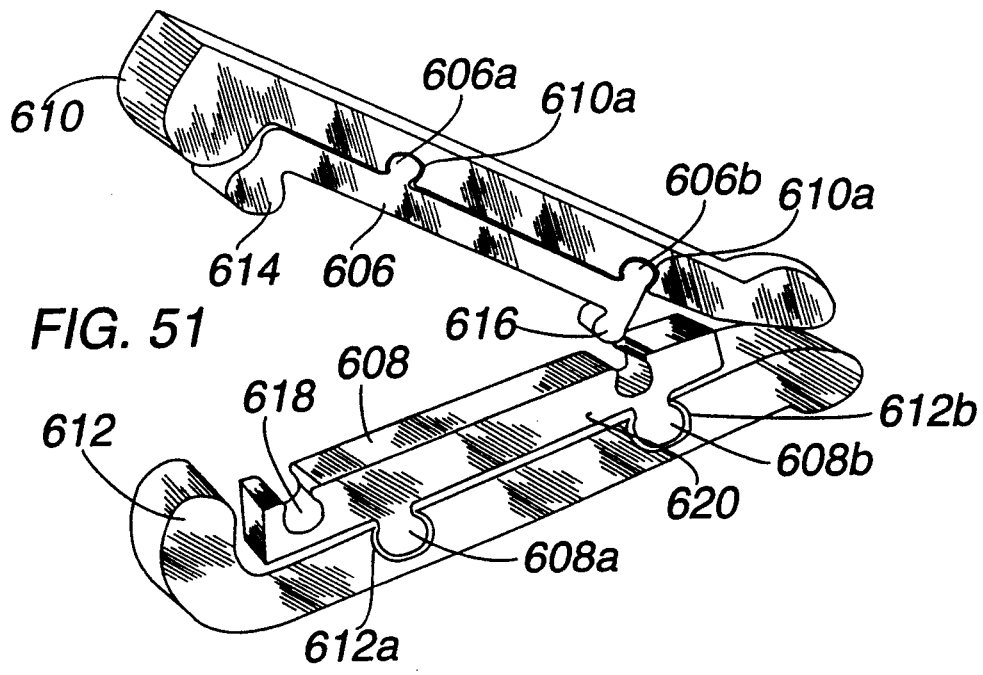
FIG. 51 is a schematic side perspective view, on an enlarged scale, of a modified staple with two leg portions attached to respective forceps jaws, in accordance with the present invention.

FIG. 51 shows a staple with two leg portions 606 and 608 temporarily attached to respective staple applying forceps jaws 610 and 612 via pairs of snap-lock projections 606a, 606b and 608a, 608b which are releasably seated in respective recesses 610a, 610b and 612a, 612b in forceps jaws 610 and 612. Staple leg portion 606 is provided with beads or ribs 614 and 616 for interlocking with respective grooves or recesses 618 and 620 in staple leg portion 608.

Figure 52:
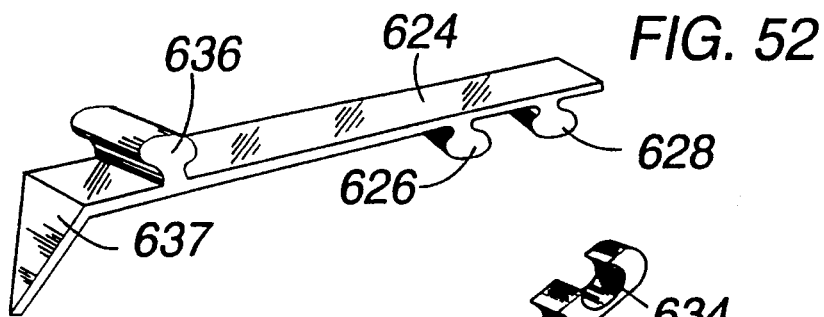
FIGS. 52 and 53 are schematic side perspective views, on an enlarged scale, of a pair of cooperating leg portions of a surgical staple in accordance with the present invention, for use in endoscopic and/or laparoscopic procedures.
Figure 53:
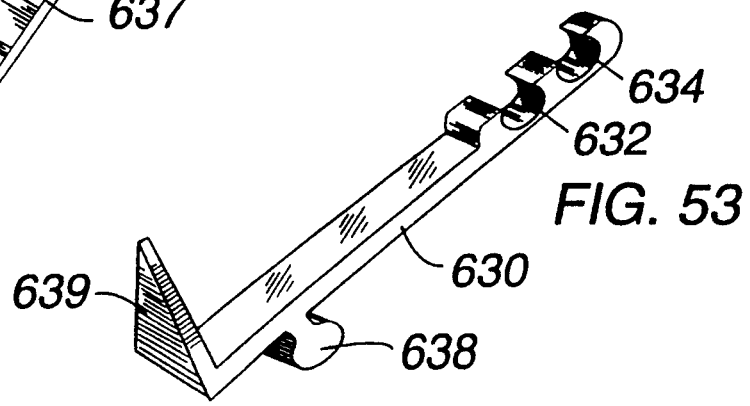
Figure 54:
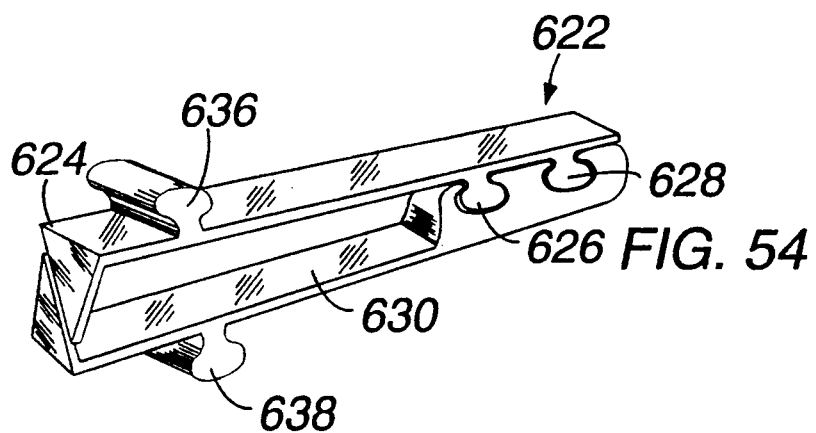
FIG. 54 is a schematic side perspective view, on an enlarged scale, of the cooperating staple leg portions of FIGS. 52 and 53 connected to one another.

As illustrated in FIGS. 52-54, another endoscopic or laparoscopic staple 622 includes a first leg 624 provided with a pair of locking elements 626 and 628 in the form of beads or ribs and a second leg 630 provided with a pair of second locking elements 632 and 634 in the form of grooves or recesses. Beads 626 and 628 cooperate with recesses 632 and 634 to maintain the staple in a closed postfiring configuration shown in FIG. 54. Beads 626 and 628 are both located at a proximal end of staple leg 624. Similarly, recesses 632 and 634 are disposed at the proximal end of staple leg 630.

Staple leg portions 624 and 630 are maintained spaced from one another in a prefiring configuration by a partition, e.g., a membrane (not shown), extending longitudinally through a tubular magazine or staple holder, e.g., holder 244 in FIGS. 24B and 24C. The membrane serves to divide a biopsy channel of an endoscope or laparoscope into two parallel channels, one for guiding a plurality of first staple legs 624 and the other for guiding a plurality of second staple legs 630.

Staple leg portions 624 and 630 are provided with latching elements 636 and 638 in the form of knob-like ribs which are releasably attachable to forceps jaws (see, e.g., FIG. 48) for controlling staple opening and closure steps during a stapling operation.

At a distal end, staple leg portions 624 and 630 are formed with inwardly turned teeth or fingers 637 and 639.

Figure 55:
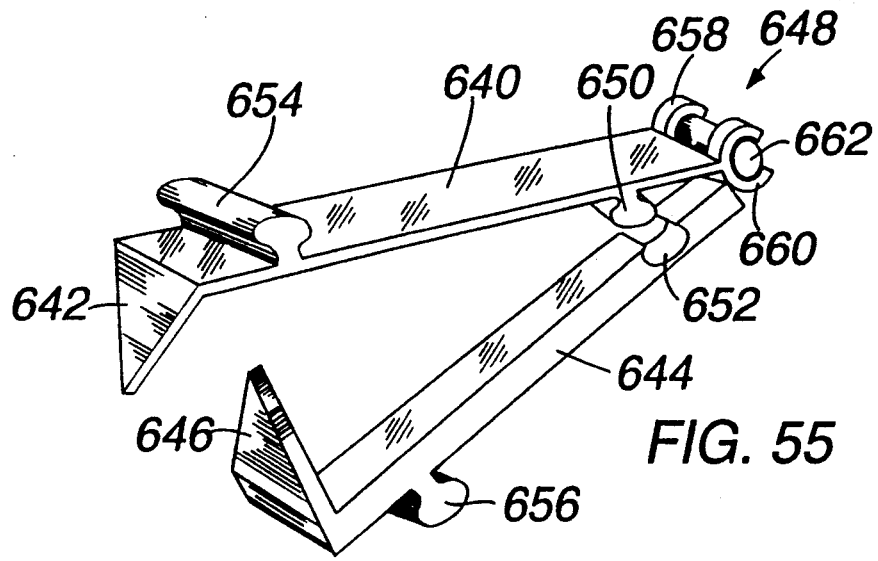
FIG. 55 is a schematic side perspective view, on an enlarged scale, of yet a further surgical staple in accordance with the present invention, for use in endoscopic and/or laparoscopic procedures.

As depicted in FIG. 55, another endoscopic or laparoscopic staple comprises a first leg 640 provided at a forward or distal end with an inwardly turned finger 642, a second leg 644 also provided at a forward or distal end with an inwardly turned finger 646, and a hinge 648 joining the first leg and the second leg to one another. Proximate to hinge 648, legs 640 and 644 are also provided with male and female locking elements 650 and 652 which are designed to cooperate with one another to maintain the staple in a closed postfiring configuration. Prior to an endoscopic or laparoscopic stapling operation, the staple of FIG. 55 is disposed in a closed prefiring configuration inside a biopsy channel of an endoscope or in a laparoscopic tubular member, wherein at least one staple leg 640 or 644 or one of the staple locking elements 650 or 652 is deformed to prevent cooperation of the locking elements.

Staple legs 640 and 644 are provided with latching elements in the form of knob-like projections 654 and 656. Projections 654 and 656 are removably seatable in recesses in forceps jaws (see FIG. 48) to enable a pivoting of legs 640 and 644 away from one another and about hinge 648 during a staple opening operation. Alternatively, the latching elements on staple legs 640 and 644 may take the form of eyelets or loops (see FIG. 44).

Hinge 648 is a rotary type hinge essentially free of internal stresses. More specifically, hinge 648 includes a pair of slotted sleeve-type elements 658 and 660 on staple leg 640 and a shaft or pin type element 662 on leg 644. Pin 662 is inserted through slotted sleeves 658 and 660.

Figure 56:
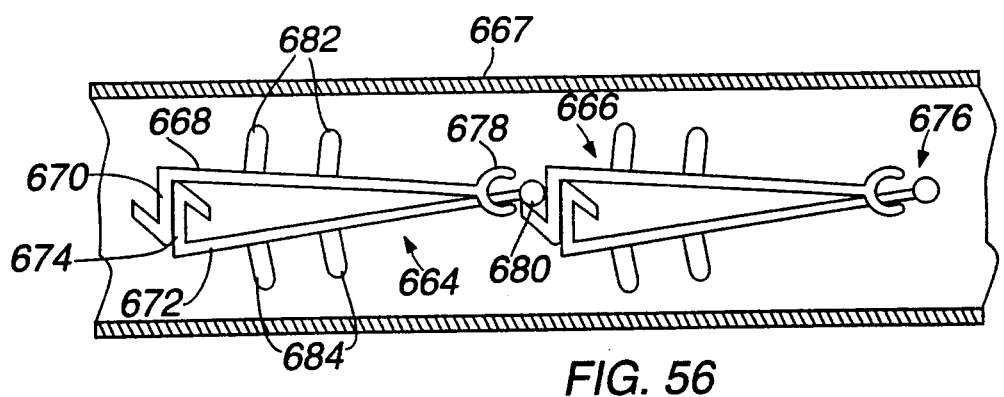
FIG. 56 is a schematic side elevational view, on an enlarged scale, of two surgical staples inside a biopsy tube or channel, in an endoscopic or laparoscopic stapling device, in accordance with the present invention.

As illustrated in FIG. 56, an endoscopic or laparoscopic surgical staple assembly comprises a plurality of staples 664 and 666 seated in a tubular member 667. Each staple 664, 666 includes a first leg 668 provided at a distal end with a locking element in the form of a hook 670 and a second leg 672 provided at a distal end with a locking element 674 also in the form of a hook. Legs 668 and 672 are couplable to one another at a proximal end by a hinge 676 which includes a slotted sleeve element 678 on one leg 668 and, on the other leg 672, a pin 680 receivable into the slotted sleeve element for pivotably joining the first leg and the second leg to one another. Staples 664 and 666 are designed so that legs 668 and 672 of each staple can be joined to one another at hinge 676 during a stapling operation. Accordingly, in a prefiring configuration, the legs 668 and 672 of each staple 664, 666 are separated and longitudinally staggered from one another. This staggering prevents hooks 670 and 674 from locking the staple prematurely.

Staple legs 668 and 672 are provided with latching elements 682 and 684 for enabling a forceps to spread the legs apart during a staple opening operation.

Upon a seating of a distal-most staple 664 in a forceps, and an opening motion of the forceps jaws, staple leg 672 is shifted distally relative to staple leg 668, whereby pin 680 is inserted into sleeve element 678 to couple legs 668 and 672 at a proximal end.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A surgical staple assembly comprising:
   a staple including:
   a first leg provided with a first locking element;
   a second leg provided with a second locking element; and
   a hinge joining said first leg and said second leg to one another, said first locking element and said second locking element being adapted to cooperate with one another to maintain the staple in a closed postfiring configuration; and
   means in contact with said staple for maintaining the staple in a closed prefiring configuration wherein at least one of said first leg, said second leg, said first locking element and said second locking element is deformed to prevent cooperation of said first locking element and said second locking element.

2. The surgical staple assembly set in claim 1, further comprising means on said first leg and said second leg for enabling said first leg and said second leg to be pivoted away from one another and about said hinge during a staple opening operation.

3. The surgical staple assembly set forth in claim 2 wherein said means for enabling includes loop-shaped elements.

4. The surgical staple assembly set forth claim 2 wherein said means for enabling includes knob-like projections.

5. The surgical staple assembly set in claim 2 wherein said means for enabling includes knob-shaped recesses.

6. The surgical staple assembly set forth in claim 1 wherein said hinge is a rotary type hinge essentially free of internal stresses.

7. The surgical staple assembly set forth in claim 6 wherein said hinge includes a sleeve-type element on one of said first leg and said second leg and a pin type element on the other of said first leg and said second leg, said pin being inserted at least partially into said sleeve.

8. The surgical staple assembly set forth in claim 1 wherein said means for maintaining includes a tubular member surrounding the staple.

9. The surgical staple assembly set forth in claim 1 wherein said first locking element and said second locking element are disposed proximately to said hinge.

10. The surgical staple assembly set forth in claim 1 wherein said first locking element and said second locking element are disposed at ends of said first leg and said second leg opposite said hinge.

11. A surgical staple assembly comprising:
a staple including:
(i) a first leg provided with a first locking element;
(ii) a second leg provided with a second locking element, said first locking element and said second locking element being adapted to cooperate with one another to maintain the staple in a closed postfiring configuration; and
(iii) hinge means including cooperating elements on said first leg and said second leg for pivotably joining said first leg and said second leg to one another; and
means for maintaining said staple in a closed prefiring configuration wherein said first leg and said second leg are staggered with respect to one another so that said first locking element and said second locking element are spaced from one another to prevent interlocking thereof and wherein said cooperating elements are spaced from one another.

12. The surgical staple assembly set forth in claim 11 wherein said staple is disposed in said means for maintaining.

13. The surgical staple assembly set forth in claim 12 wherein said means for maintaining includes a tubular member.

14. The surgical staple assembly set forth in claim 11, further comprising means on said first leg and said second leg for enabling said first leg and said second leg to be moved away from one another during a staple opening operation.

15. The surgical staple assembly set forth in claim 11 wherein said cooperating elements include a slotted sleeve-type element on one of said first leg and said second leg and a pin type element on the other of said first leg and said second leg, said pin being insertable at least partially into said sleeve.

16. The surgical staple assembly set forth in claim 11 wherein said first locking element and said second locking element are disposed proximately to said hinge means.

17. The surgical staple assembly set forth in claim 11 wherein said first locking element and said second locking element are disposed at ends of said first leg and said second leg opposite said hinge means.

18. A surgical staple assembly comprising:
a staple including:
a first leg portion provided with a pair of spaced first locking elements; and
a second leg portion provided with a pair of spaced second locking elements, said first locking elements and said second locking elements being adapted to cooperate with one another to maintain the staple in a closed postfiring configuration; and
means for maintaining said staple in a prefiring configuration wherein said first leg portion and said second leg portion are spaced with respect to one another to prevent interlocking of said first locking elements and said second locking elements.

19. The surgical staple assembly set forth in claim 18 wherein said staple is disposed in said means for maintaining.

20. The surgical staple assembly set forth in claim 19 wherein said means for maintaining includes a tubular member.

21. The surgical staple assembly set forth in claim 18, further comprising means on said first leg and said second leg for enabling said first leg and said second leg to be moved away from one another during a staple opening operation.

22. The surgical staple assembly set forth in claim 18 wherein said first locking elements are disposed proximately to each other and to one end of said first leg portion and wherein said second locking elements are disposed proximately to each other and to one end of said second leg portion.

23. The surgical staple assembly set forth in claim 18 wherein said first locking elements are disposed at opposite ends of said first leg portions and wherein said second locking elements are disposed at opposite ends of said second leg portion.

24. A surgical device utilizable with an endoscope or rigid tubular member for performing an endoscopic or laparoscopic stapling operation, comprising:
a forceps member slidably disposable inside a biopsy channel of an endoscopic or laparoscopic instrument;
actuating means operatively connected to said forceps member for manipulating jaws of said forceps member between opened and closed positions;
a staple having a pair of legs and a hinge joint for coupling said legs at one end to one another so that said legs swing substantially freely about said joint, said legs being provided with respective locking elements which cooperate with one another to maintain the staple in a closed postfiring configuration, said staple being disposed in a closed prefiring configuration between said jaws when said jaws are in a closed position inside the biopsy channel of the endoscopic or laparoscopic instrument; and
locking means on said legs and said jaws for temporarily locking said legs to said jaws at least during an opening motion of said jaws, whereby said legs are pivoted about said hinge joint to open said staple from said prefiring configuration.

25. The surgical device set forth in claim 24 wherein said locking means includes longitudinally slidable rods.

26. The surgical device set forth in claim 25 wherein said locking means further includes aperture forming elements on said legs.

27. The surgical staple set forth in claim 24 wherein said locking means includes snap-lock-type projections and cooperating recesses.

28. The surgical device set forth in claim 24 wherein at least one of said legs and said locking elements is deformed in said prefiring configuration of said staple to prevent cooperation of said locking elements.

29. The surgical device set forth in claim 24 wherein said legs are staggered with respect to one another in said prefiring configuration of said staple to prevent cooperation of said locking elements.

* * * * *